United States Patent
Richer et al.

(10) Patent No.: US 8,507,195 B2
(45) Date of Patent: Aug. 13, 2013

(54) MIRNAS DYSREGULATED IN TRIPLE-NEGATIVE BREAST CANCER

(75) Inventors: Jennifer Richer, Aurora, CO (US);
Dawn Cochrane, Aurora, CO (US);
Steven M. Anderson, Aurora, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 13/390,460

(22) PCT Filed: Aug. 16, 2010

(86) PCT No.: PCT/US2010/045574
§ 371 (c)(1), (2), (4) Date: Apr. 30, 2012

(87) PCT Pub. No.: WO2011/022316
PCT Pub. Date: Feb. 24, 2011

(65) Prior Publication Data
US 2012/0214864 A1 Aug. 23, 2012

Related U.S. Application Data

(60) Provisional application No. 61/235,486, filed on Aug. 20, 2009.

(51) Int. Cl.
*C12Q 1/68* (2006.01)

(52) U.S. Cl.
USPC ............................... 435/6; 435/325; 435/375

(58) Field of Classification Search
None
See application file for complete search history.

(56) References Cited

U.S. PATENT DOCUMENTS

| | | |
|---|---|---|
| 2007/0248659 A1 | 10/2007 | Shanahan et al. |
| 2008/0103208 A1 | 5/2008 | Ossovskaya et al. |
| 2009/0163564 A1 | 6/2009 | Borden et al. |
| 2010/0179213 A1 | 7/2010 | Patrawala et al. |

FOREIGN PATENT DOCUMENTS

| | | |
|---|---|---|
| WO | WO 2007/109026 | 9/2007 |
| WO | WO 2007/112754 | 10/2007 |
| WO | WO 2009/012263 | 1/2009 |

OTHER PUBLICATIONS

"Comprehensive miRNA Research Technologies," available at <www.quiagen.com> updated Apr. 2007.
Blenkiron et al., "MicroRNA expression profiling of human breast cancer identifies new markers of tumor subtype," *Genome Biology*, 8:R214, 2007.
Cochrane et al., "MicroRNAs link estrogen receptor alpha status and dicer levels in breast cancer," *Hormones and Cancer*, 1(6): 306-319, 2010.
International Search Report and Written Opinion issued in PCT/US2100/045574, dated Oct. 15, 2010.

*Primary Examiner* — Kimberly Chong
(74) *Attorney, Agent, or Firm* — Parker Highlander, PLLC

(57) ABSTRACT

The invention provides methods of diagnosing and treating cancer in a subject. The inventors have identified a series of dysregulated miRNAs that are indicative of triple-negative breast cancer. In some embodiments, the invention further provides for the administration of a cancer therapy to the subject.

14 Claims, 8 Drawing Sheets

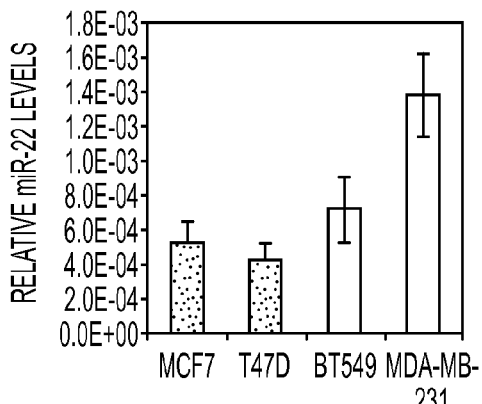

FIG. 2A

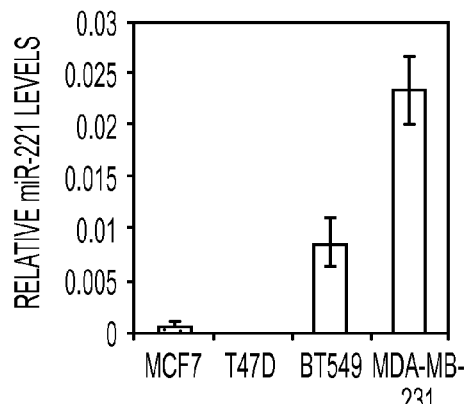

FIG. 2B

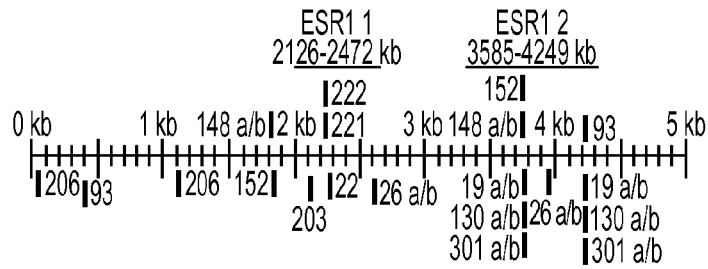

| miRNA | TARGET POSITION ON 3' UTR | PREDITIVE ALGORITHM |
|---|---|---|
| miR-19 a/b | 3765, 4219 | TARGETSCAN, PICTAR |
| miR-22 | 2292 | TARGETSCAN, PICTAR, MIRANDA |
| miR-26 a/b | 2606, 3975 | TARGETSCAN, PICTAR |
| miR-93 | 380, 4212 | PICTAR, MIRANDA |
| miR-130 a/b | 3766, 4210 | TARGETSCAN, PICTAR, MIRANDA |
| miR-148 a/b | 1817, 3767 | TARGETSCAN, PICTAR, MIRANDA |
| miR-152 | 1817, 3767 | TARGETSCAN, PICTAR, MIRANDA |
| miR-203 | 2166 | TARGETSCAN, MIRANDA |
| miR-206 | 87, 1137 | ADAMS ET AL |
| miR-221 | 2253 | TARGETSCAN, PICTAR, MIRANDA |
| miR-222 | 2253 | TARGETSCAN, PICTAR, MIRANDA |
| miR-301 a/b | 3760, 4210 | TARGETSCAN, PICTAR, MIRANDA |

FIG. 2C

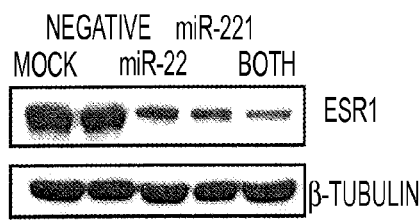

FIG. 2D

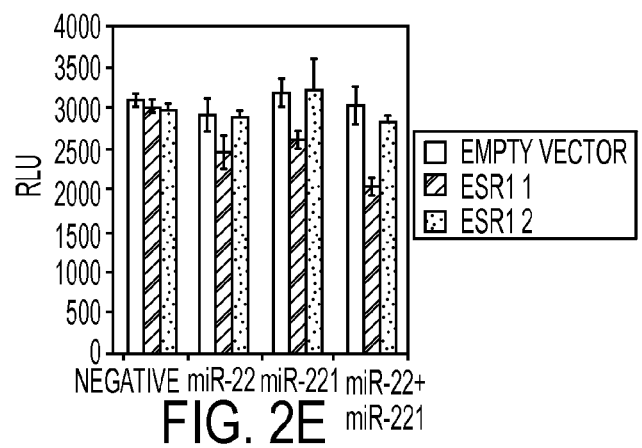

FIG. 2E

SEQUENCE LISTING

<160> NUMBER OF SEQ ID NOS: 14

<210> SEQ ID NO 1
<211> LENGTH: 22
<212> TYPE: RNA
<213> ORGANISM: Artificial Sequence
<220> FEATURE:
<223> OTHER INFORMATION: Synthetic primer

<400> SEQUENCE: 1
aacuggcccu caaagucccg cu                                                22

<210> SEQ ID NO 2
<211> LENGTH: 22
<212> TYPE: RNA
<213> ORGANISM: Artificial Sequence
<220> FEATURE:
<223> OTHER INFORMATION: Synthetic primer

<400> SEQUENCE: 2
uggcaguguc uuagcugguu gu                                                22

<210> SEQ ID NO 3
<211> LENGTH: 23
<212> TYPE: RNA
<213> ORGANISM: Artificial Sequence
<220> FEATURE:
<223> OTHER INFORMATION: Synthetic primer

<400> SEQUENCE: 3
cagugcaaua guauugucaa agc                                               23

<210> SEQ ID NO 4
<211> LENGTH: 22
<212> TYPE: RNA
<213> ORGANISM: Artificial Sequence
<220> FEATURE:
<223> OTHER INFORMATION: Synthetic primer

<400> SEQUENCE: 4
ucagugcacu acagaacuuu gu                                                22

<210> SEQ ID NO 5
<211> LENGTH: 22
<212> TYPE: RNA
<213> ORGANISM: Artificial Sequence
<220> FEATURE:
<223> OTHER INFORMATION: Synthetic primer

<400> SEQUENCE: 5
uagcagcaca ucaugguuua ca                                                22

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccactagtgt catttatgcc t                                                 21

<210> SEQ ID NO 7
<211> LENGTH: 20
<212> TYPE: DNA

<213> ORGANISM: Artificial Sequence
<220> FEATURE:
<223> OTHER INFORMATION: Synthetic primer

<400> SEQUENCE: 7
ctcaagcttc cttccactgt                                              20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ccactagtct caactggagc a                                            21

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ctcaagctta caggtgctcg                                              20

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cggggttttg agggcgagat ga                                           22

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
agttttgcag gtttgcatcc agc                                          23

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
actgcattat gagcacttaa ag                                           22

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
aaaagtgctt acagtgcagg tag                                          23

```
<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
agggacggga cgcggtgcag tg                                              22
```

MIRNAS DYSREGULATED IN TRIPLE-NEGATIVE BREAST CANCER

This application is a national phase application under 35 U.S.C. §371 of International Application No. PCT/US2010/045574 filed Aug. 16, 2010, which claims benefit of priority to U.S. Provisional Application Ser. No. 61/235,486 filed Aug. 20, 2009. The entire text of each of the above-referenced disclosures is specifically incorporated herein by reference without disclaimer.

This invention was made with government support under Grant Number W81XWH-09-1-0124 awarded by Army/Medical Research Material and Command. The government has certain rights in this invention.

Pursuant to 37 C.F.R. 1.821(c), a sequence listing is submitted herewith as an ASCII compliant text file named "UTECP0021US_ST25.txt," created on Feb. 5, 2013 and having a size of ~3 kb. The content of the aforementioned file is hereby incorporated by reference in its entirety.

BACKGROUND OF THE INVENTION

I. Field of the Invention

The present invention relates generally to the fields of oncology, molecular biology, and medicine. More particularly, the invention relates to use of certain miRNAs that are dysregulated in so-called "triple-negative" breast cancer as both diagnostic and therapeutic targets.

II. Description of Related Art

MicroRNAs (miRNAs) are small RNA molecules, 19-25 nucleotides in length. miRNAs are not translated, instead they serve as regulators of mRNA expression (Ouellet et al., 2006). For the most part, miRNAs bind to complementary regions in target mRNA 3'UTRs and either cause mRNA degradation or prevent its translation (Engels and Hutvagner, 2006). Generally, one observes a decrease of the target at the protein level; however, there is some emerging evidence that miRNAs can also cause upregulation of their targets. Individual miRNAs have been found to be expressed in cell-specific manner, at specific developmental stages, as well as differentially expressed in disease states (Yi et al., 2008; Sempere et al., 2007). Importantly, miRNAs have been implicated as playing roles as oncogenes and tumor suppressors (Cho, 2007; Cowland et al., 2007). While there are miRNAs that are found to be overexpressed in cancers, many appear to be lost and they tend to localize to fragile sites (Calin et al., 2004).

Breast cancer is a heterogeneous disease which can be grouped into several different subtypes. One of the most well-differentiated subtypes is Luminal A, which encompasses cancers that retain their hormone receptors (estrogen and progesterone receptors). On the other end of the spectrum, there is the triple-negative (TN)/basal subtype. TN cancers have lost expression of their hormone receptors and do not overexpress HER2/neu. TN breast cancers are poorly-differentiated, have often undergone epithelial to mesenchymal transition (EMT) and have poor a prognosis. Thus, improved methods to distinguish these types of cancers at early stages are urgently needed.

SUMMARY OF THE INVENTION

Thus, in accordance with the present invention, there is provided a method of identifying "triple-negative" breast cancer in a subject comprising (a) obtaining a sample from the subject; and (b) assessing the sample for one or more miRNAs selected from the group consisting of miR-193b, miR-34a, miR-301a, miR-148a and/or miR-15b; wherein decreased levels of one or more of miR-193b, miR-34a, miR-301a, miR-148a and/or miR-15b, as compared to a luminal breast cancer, indicates that the subject has a "triple-negative" breast cancer. The sample may be a biopsy or resected tumor tissue. Assessing may comprise microarray hybridization.

One, two, three, four or all five of the miRNAs may be assessed. One, two, three, four or five of the miRNAs may be decreased. The subject may be determined not to have "triple-negative" breast cancer, and the method may further comprise administering to the subject a treatment for ER-positive breast cancer. Alternatively, the subject may be determined to have "triple-negative" breast cancer, and the method may further comprise administering to the subject a treatment for "triple-negative" breast cancer.

The subject may exhibit reduced miR-193b, and optionally, the subject may be treated with a fatty acid synthase inhibitor, such as miR-193b, c75 or Orlistat®. The subject may exhibit reduced miR-34a, and optionally, the subject may be treated with miR-34a. The subject may exhibit reduced miR-301a, and optionally, the subject may be treated with miR-301a. The subject may exhibit reduced miR-148a, and optionally, the subject may be treated with miR-148a. The subject may exhibit reduced miR-15b, and optionally, the subject may be treated with miR-15b.

In another embodiment, there is provided a method of treating a subject with "triple-negative" breast cancer comprising providing to the subject one or more miRNAs selected from the group consisting of miR-193b, miR-34a, miR-301a, miR-148a and/or miR-15b, and/or a mimic therefor. Providing may comprise administration into a vein, artery, tumor or tumor vasculature. The one or more miRNAs may be formulated in a lipid vehicle. Providing may comprise administering to the subject an expression vector that expresses on or more of the miRNAs, such as a viral expression vector. One, two, three, four or five of the miRNAs, or mimic(s), may be provided. One, two, three, four or five of the miRNAs, or mimic(s), may be provided more than once. The method may further comprise treating the subject with chemotherapy, radiotherapy, toxin therapy, hormone therapy or immunotherapy.

In still yet another embodiment, there is provides a method of treating a subject with "triple-negative" breast cancer comprising providing to the subject miR-200c in combination with one or more agents that reduces the expression or function of miR-221/222 and/or miR-29a. Providing may comprise administration into a vein, artery, tumor or tumor vasculature. The miR-200c may formulated in a lipid vehicle, and/or may be provided to the subject by administering an expression vector that expresses miR-200c, such as a viral expression vector. The one or more agents that reduce the expression or function of miR-221/222 and/or miR-29a may be an antagomir of miR-221/222 or miR-29a, or both. The miRNAs and/or antagomirs may be provided more than once, including where each of miR-200c and antagomirs of miR-221/222 and miR-29a are provided more than once. The method may further comprise treating the subject with chemotherapy, radiotherapy, toxin therapy, hormone therapy or immunotherapy.

Any embodiment discussed with respect to one aspect of the invention applies to other aspects of the invention as well.

The embodiments in the Examples section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

(FIG. 1A) Heatmap from miRNA microarray analysis of luminal (MCF7 and T47D) versus triple-negative (MDA-MB-231 and BT549) cell lines. Biological duplicate samples for each cell line were hybridized to Agilent miRNA microarrays. Shown are miRNAs that exhibit 1.5-fold or greater differential expression between the luminal and triple-negative cell lines. Graphical representation of miRNAs lower in the triple-negative cell lines versus luminal (FIG. 1B) or higher in the triple-negative versus luminal (FIG. 1C). Error bars represent the standard error of the mean for the four samples in each group.

FIGS. 2A-E—miR-22 and miR-221 work co-operatively to downregulate the estrogen receptor. Real-time PCR to validate the miRNA microarrays by amplification of miR-22 (FIG. 2A) and miR-221 (FIG. 2B) in two luminal (MCF7 and T47D) and two triple-negative (BT549 and MDA-MB-231) cell lines. Shown are the averages of three replicate samples and error bars represent the standard error of the means. (FIG. 2C) Map of 3' UTR of the estrogen receptor (ESR1) showing putative miRNA binding sites. (FIG. 2D) Western blot of MCF7 cells treated with a mock transfection, a scrambled negative control, miR-22 mimic, a miR-221 mimic or a combination of both mimics. Protein was harvested 72 h after transfection. The blot was probed for ESR1α and β-tubulin as a loading control. The experiment was repeated 3 times; shown is a representative blot. (FIG. 2E) The region of the ESR1 3' UTR containing the miR-22 and 221 binding sites (ESR1-1) or a region of the ESR1 3'UTR not containing any miR-22 or miR-221 binding sites (ESR1-2) was cloned into the 3' UTR region of a luciferase reporter vector. These constructs or the empty vector was transfected into cells treated with a scrambled negative control, the miR-22 mimic, the miR-221 mimic or both and a luciferase assay was performed. Error bars represent the standard error of the mean for 5 replicates.

(FIG. 3A) MiR-193b is expressed at higher levels in luminal A cells by QPCR. (FIG. 3B) Transfection of a miR-193b mimic into BT549 (triple negative) cells for 72 h causes a decrease in FASN and an induction of apoptosis. (FIG. 3C) No apoptosis is observed when miR-193b is transfected into MCF10A (normal immortalized) cells.

(FIG. 4C) Shown are the relative miRNA levels for miR-19b, miR-20a and miR-106a after 48 h of treatment, and miR-92b* after 24 h of treatment.

(FIG. 5A) Real-time PCR for miR-7 was performed in two luminal cell lines (MCF7 and T47D) and two triple-negative cell lines (BT549 and MDA-MB-231). (FIG. 5B) Real-time PCR for miR-7 in cells that had been treated with the ethanol vehicle control, 10 nM estradiol (E2) or estradiol and 1 µM ICI (E2+ICI) for 24 h. Shown are the averages of three replicate samples and error bars represent the standard error of the means. (FIG. 5C) MDA-MB-231 cells were mock transfected, transfected with a scrambled negative control or a miR-7 mimic for 72 h. Protein was harvested and used for immunoblotting. The blots were probed for EGFR, IGF1Rβ, InRβ, IRS-1, IRS-2, phospho-MAPK and MAPK which was used as a loading control.

DESCRIPTION OF ILLUSTRATIVE EMBODIMENTS

Figure 1A:
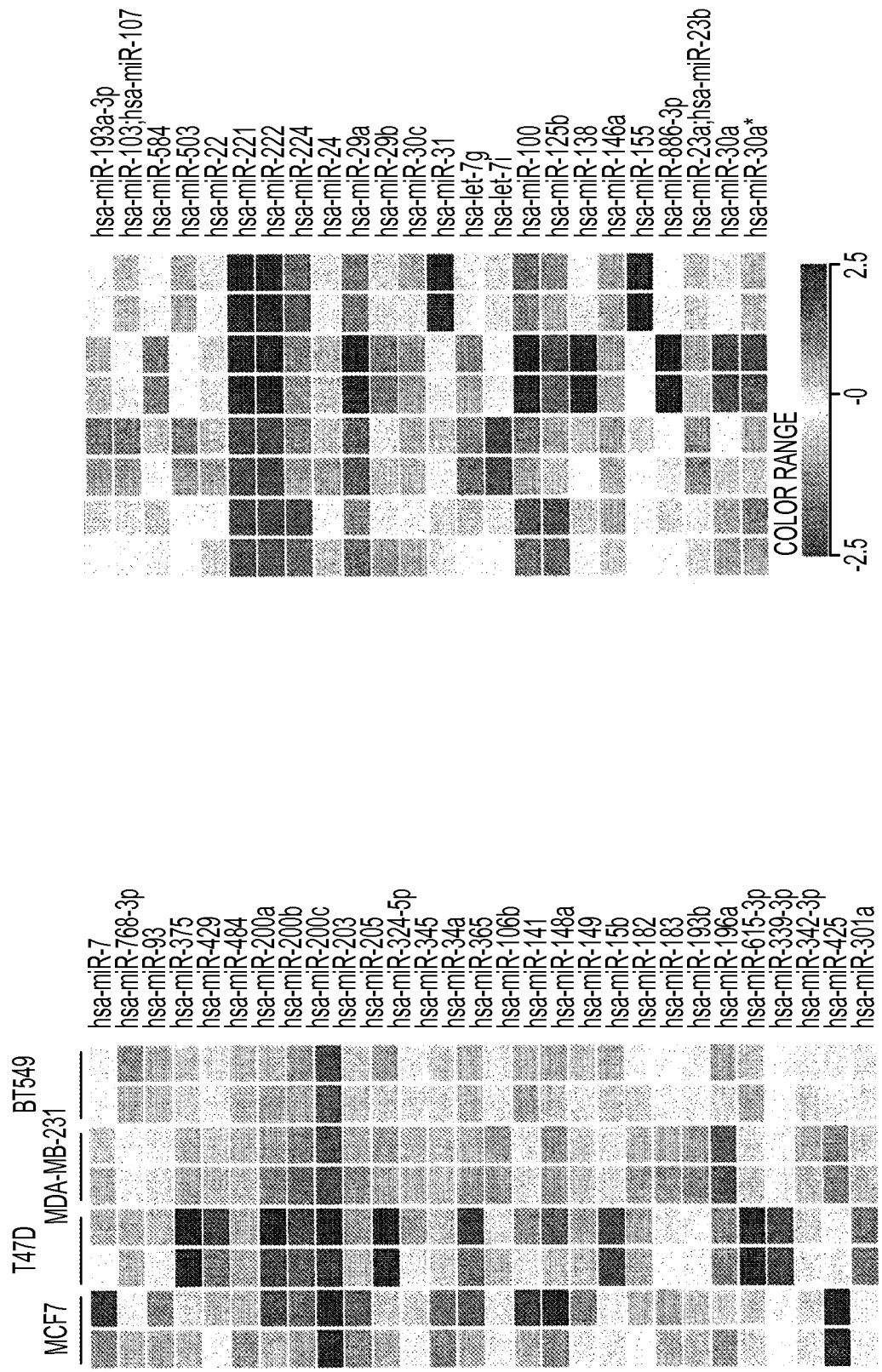
FIGS. 1A-C—miRNAs differentially expressed in luminal versus triple-negative breast cancer cell lines.

Recently, the inventors' laboratory and others have demonstrated that miRNA-200c (miR-200c) and its family members are high in normal epithelial cells and low-grade cancer cells that retain epithelial characteristics (Hurteau et al., 2007; Park et al., 2008; Gregory et al., 2008; Burk et al., 2008; Korpal et al., 2008; Hurteau et al., 2009; Taylor and Gercel-Taylor, 2008; Cochrane et al., 2009). Global profiling has established that miRNAs differ between breast cancer and normal breast and can discriminate between the molecular subtypes of breast cancer (Mattie et al., 2006; Iorio et al., 2005; Blenkiron et al., 2007; Lowery et al., 2008; Iorio et al., 2008. However, tumors are heterogeneous and contain stromal and epithelial cells as well as infiltrating immune cells. Therefore, the inventors performed miRNA profiling of two well-differentiated estrogen receptor α (ESR1)-positive breast cancer cell lines, MCF-7 and T47D, which belong to the luminal A molecular subtype, as compared to two de-differentiated, ESR1-negative lines, MDA-MB-231 and BT549, belonging to the TN subtype. The goal was to identify additional miRNAs associated with EMT.

Overall, the inventors found that more miRNAs are expressed at higher levels in the well-differentiated luminal subtype. Indeed, they found that the miR-200 family members are the most differentially-expressed miRNAs, higher in luminal (epithelial) cells. This family is well-known to control EMT by directly repressing ZEB1/2 (Hurteau et al., 2007; Park et al., 2008; Gregory et al., 2008; Burk et al., 2008; Korpal et al., 2008; Hurteau et al., 2009; Cochrane et al., 2009), a transcriptional repressor of E-cadherin, as well as other mesenchymal genes (Cochrane et al., 2009). The inventors also found that after the miR-200 family, miR-193b is the next most highly differentially-expressed miRNA higher in luminal A cells as compared to triple-negative. They also observed that increasing miR-193 in triple-negative breast cancer cells represses expression of FASN protein and increases apoptosis.

In contrast, fewer miRNAs are more abundant in triple-negative cells than luminal. Those that are overexpressed include miR-221 and miR-22 which target ESR1 (Zhao et al., 2008; Miller et al., 2008; Pandey and Picard, 2009). miR-221/222 is 90-fold higher in triple-negative breast cancer cells as compared to luminal, and it and miR-22 (2-fold higher in triple-negative) both target ESR1, binding to two closely positioned sites in the ESR1 3'UTR.

In addition to screening for miRNA differentially expressed in ESR1-positive versus-negative cells, the inventors identified miRNAs regulated by estradiol in ESR1-positive MCF-7 breast cancer cells. These results overlap somewhat with those recently identified by Bhat-Nakshatri et al. (2009) using a different platform. However, the inventors have made the important observation that miRNAs such as miR-7 are both regulated by estradiol and also constitutively higher in ESR1-positive cells than ESR1-negative cells even in estradiol-free conditions. Furthermore, the inventors' findings suggest that overexpression of growth factor receptors such as EGFR and IGF1R in TNBC may be a result of loss of ESR1-regulated miRNA such as miR-7, which may play an important role in fine tuning the appropriate expression of growth factor receptors.

These and other aspects of the invention are described in further detail below.

BREAST CANCER

A. Background

Breast cancer is a cancer that starts in the breast, usually in the inner lining of the milk ducts or lobules. There are different types of breast cancer, with different stages (spread), aggressiveness, and genetic makeup. With best treatment, 10-year disease-free survival varies from 98% to 10%. Treatment is selected from surgery, drugs (chemotherapy), and radiation. In the United States, there were 216,000 cases of invasive breast cancer and 40,000 deaths in 2004. Worldwide, breast cancer is the second most common type of cancer after lung cancer (10.4% of all cancer incidence, both sexes counted) and the fifth most common cause of cancer death. In 2004, breast cancer caused 519,000 deaths worldwide (7% of cancer deaths; almost 1% of all deaths). Breast cancer is about 100 times as frequent among women as among men, but survival rates are equal in both sexes.

B. Symptoms

The first symptom, or subjective sign, of breast cancer is typically a lump that feels different from the surrounding breast tissue. According to the *The Merck Manual*, more than 80% of breast cancer cases are discovered when the woman feels a lump. According to the American Cancer Society, the first medical sign, or objective indication of breast cancer as detected by a physician, is discovered by mammogram. Lumps found in lymph nodes located in the armpits can also indicate breast cancer. Indications of breast cancer other than a lump may include changes in breast size or shape, skin dimpling, nipple inversion, or spontaneous single-nipple discharge. Pain ("mastodynia") is an unreliable tool in determining the presence or absence of breast cancer, but may be indicative of other breast health issues.

When breast cancer cells invade the dermal lymphatics—small lymph vessels in the skin of the breast—its presentation can resemble skin inflammation and thus is known as inflammatory breast cancer (IBC). Symptoms of inflammatory breast cancer include pain, swelling, warmth and redness throughout the breast, as well as an orange-peel texture to the skin referred to as "peau d' orange." Another reported symptom complex of breast cancer is Paget's disease of the breast. This syndrome presents as eczematoid skin changes such as redness and mild flaking of the nipple skin. As Paget's advances, symptoms may include tingling, itching, increased sensitivity, burning, and pain. There may also be discharge from the nipple. Approximately half of women diagnosed with Paget's also have a lump in the breast.

Occasionally, breast cancer presents as metastatic disease, that is, cancer that has spread beyond the original organ. Metastatic breast cancer will cause symptoms that depend on the location of metastasis. Common sites of metastasis include bone, liver, lung and brain. Unexplained weight loss can occasionally herald an occult breast cancer, as can symptoms of fevers or chills. Bone or joint pains can sometimes be manifestations of metastatic breast cancer, as can jaundice or neurological symptoms. These symptoms are "non-specific," meaning they can also be manifestations of many other illnesses.

C. Risk Factors

The primary risk factors that have been identified are sex, age, childbearing, hormones, a high-fat diet, alcohol intake, obesity, and environmental factors such as tobacco use, radiation and shiftwork. No etiology is known for 95% of breast cancer cases, while approximately 5% of new breast cancers are attributable to hereditary syndromes. In particular, carriers of the breast cancer susceptibility genes, BRCA1 and BRCA2, are at a 30-40% increased risk for breast and ovarian cancer, depending on in which portion of the protein the mutation occurs. Experts believe that 95% of inherited breast cancer can be traced to one of these two genes. Hereditary breast cancers can take the form of a site-specific hereditary breast cancer-cancers affecting the breast only- or breast-ovarian and other cancer syndromes. Breast cancer can be inherited both from female and male relatives.

D. Subtypes

Breast cancer subtypes are categorized on an immunohistochemical basis. Subtype definitions are general as follows:
- normal (ER+, PR+, HER2+, cytokeratin 5/6+, and HER1+)
- luminal A (ER+ and/or PR+, HER2−)
- luminal B (ER+ and/or PR+, HER2+)
- triple-negative (ER−, PR−, HER2−)
- HER2+/ER−(ER−, PR−, and HER2+)
- unclassified (ER−, PR−, HER2−, cytokeratin 5/6−, and HER1−)

In the case of triple-negative breast cancer cells, the cancer's growth is not driven by estrogen or progesterone, or by growth signals coming from the HER2 protein. By the same token, such cancer cells do not respond to hormonal therapy, such as tamoxifen or aromatase inhibitors, or therapies that target HER2 receptors, such as Herceptin®. About 10-20% of breast cancers are found to be triple-negative. It is important to identify these types of cancer to that one can avoid costly and toxic effects of therapies that are unlike to succeed, and to focus on treatments that can be used to treat triple-negative breast cancer. Like other forms of breast cancer, triple-negative breast cancer can be treated with surgery, radiation therapy, and/or chemotherapy. One particularly promising approach is "neoadjuvant" therapy, where chemo- and/or radiotherapy is provided prior to surgery. Another new drug therapy is the use of poly(ADP-ribose) polymerase, or PARP inhibitors.

E. Screening and Diagnosis

While screening techniques discussed above are useful in determining the possibility of cancer, a further testing is necessary to confirm whether a lump detected on screening is cancer, as opposed to a benign alternative such as a simple cyst. In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a GP's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

Breast cancer screening is an attempt to find cancer in otherwise healthy individuals. The most common screening method for women is a combination of x-ray mammography and clinical breast exam. In women at higher than normal risk, such as those with a strong family history of cancer, additional tools may include genetic testing or breast Magnetic Resonance Imaging.

Breast self-examination was a form of screening that was heavily advocated in the past, but has since fallen into disfavor since several large studies have shown that it does not have a survival benefit for women and often causes considerably anxiety. This is thought to be because cancers that could be detected tended to be at a relatively advanced stage already, whereas other methods push to identify the cancer at an earlier stage where curative treatment is more often possible.

X-ray mammography uses x-rays to examine the breast for any uncharacteristic masses or lumps. Regular mammograms are recommended in several countries in women over a certain age as a screening tool.

Genetic testing for breast cancer typically involves testing for mutations in the BRCA genes. This is not generally a recommended technique except for those at elevated risk for breast cancer.

F. Treatments

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided to high risk and low risk cases, with each risk category following different rules for therapy. Treatment possibilities include radiation therapy, chemotherapy, hormone therapy, and immune therapy.

Targeted cancer therapies are treatments that target specific characteristics of cancer cells, such as a protein that allows the cancer cells to grow in a rapid or abnormal way. Targeted therapies are generally less likely than chemotherapy to harm normal, healthy cells. Some targeted therapies are antibodies that work like the antibodies made naturally by our immune systems. These types of targeted therapies are sometimes called immune-targeted therapies.

There are currently 3 targeted therapies doctors use to treat breast cancer. Herceptin® (trastuzumab) works against HER2-positive breast cancers by blocking the ability of the cancer cells to receive chemical signals that tell the cells to grow. Tykerb® (lapatinib) works against HER2-positive breast cancers by blocking certain proteins that can cause uncontrolled cell growth. Avastin® (bevacizumab) works by blocking the growth of new blood vessels that cancer cells depend on to grow and function.

Hormonal (anti-estrogen) therapy works against hormone-receptor-positive breast cancer in two ways: first, by lowering the amount of the hormone estrogen in the body, and second, by blocking the action of estrogen in the body. Most of the estrogen in women's bodies is made by the ovaries. Estrogen makes hormone-receptor-positive breast cancers grow. So reducing the amount of estrogen or blocking its action can help shrink hormone-receptor-positive breast cancers and reduce the risk of hormone-receptor-positive breast cancers coming back (recurring). Hormonal therapy medicines are not effective against hormone-receptor-negative breast cancers.

There are several types of hormonal therapy medicines, including aromatase inhibitors, selective estrogen receptor modulators, and estrogen receptor downregulators. In some cases, the ovaries and fallopian tubes may be surgically removed to treat hormone-receptor-positive breast cancer or as a preventive measure for women at very high risk of breast cancer. The ovaries also may be shut down temporarily using medication.

In planning treatment, doctors can also use PCR tests like Oncotype DX or microarray tests that predict breast cancer recurrence risk based on gene expression. In February 2007, the first breast cancer predictor test won formal approval from the Food and Drug Administration. This is a new gene test to help predict whether women with early-stage breast cancer will relapse in 5 or 10 years, this could help influence how aggressively the initial tumor is treated.

Radiation therapy is also used to help destroy cancer cells that may linger after surgery. Radiation can reduce the risk of recurrence by 50-66% when delivered in the correct dose.

MIRNAS

A. Background

In 2001, several groups used a novel cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets.

miRNAs are transcribed by RNA polymerase II and can be derived from individual miRNA genes, from introns of protein coding genes, or from poly-cistronic transcripts that often encode multiple, closely related miRNAs. Pre-miRNAs, generally several thousand bases long are processed in the nucleus by the RNase Drosha into 70- to 100-nt hairpin-shaped precursors. Following transport to the cytoplasm, the hairpin is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Krania, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs.

The first miRNAs were identified as regulators of developmental timing in *C. elegans*, suggesting that miRNAs, in general, might play decisive regulatory roles in transitions between different developmental states by switching off specific targets (Fatkin et al., 2000; Lowes et al., 1997). However, subsequent studies suggest that miRNAs, rather than functioning as on-off "switches," more commonly function to modulate or fine-tune cell phenotypes by repressing expression of proteins that are inappropriate for a particular cell type, or by adjusting protein dosage. miRNAs have also been proposed to provide robustness to cellular phenotypes by eliminating extreme fluctuations in gene expression (Miyata et al., 2000).

Research on microRNAs is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (reviewed in Pasquinelli, 2002). Several hundred miRNAs have been identified in *C. elegans, Drosophila*, mouse, and humans. As would be expected for molecules that regulate gene expression, miRNA levels have been shown to vary between tissues and developmental states. In addition, one study shows a strong correlation between reduced expression of two miRNAs and chronic lymphocytic leukemia, providing a possible link between miRNAs and cancer (Calin, 2002). Although the field is still young, there is speculation that miRNAs could be as important as transcription factors in regulating gene expression in higher eukaryotes.

There are a few examples of miRNAs that play critical roles in cell differentiation, early development, and cellular processes like apoptosis and fat metabolism. lin-4 and let-7 both regulate passage from one larval state to another during *C. elegans* development (Ambros, 2003). miR-14 and bantam are *drosophila* miRNAs that regulate cell death, apparently by regulating the expression of genes involved in apoptosis (Brennecke et al., 2003, Xu et al., 2003). miR-14 has also been implicated in fat metabolism (Xu et al., 2003). Lsy-6 and miR-273 are *C. elegans* miRNAs that regulate asymmetry in chemosensory neurons (Chang et al., 2004). Another animal miRNA that regulates cell differentiation is miR-181, which guides hematopoietic cell differentiation (Chen et al., 2004). These molecules represent the full range of animal miRNAs with known functions. Enhanced understanding of the functions of miRNAs will undoubtedly reveal regulatory networks that contribute to normal development, differentiation, inter- and intra-cellular communication, cell cycle, angiogenesis, apoptosis, and many other cellular processes. Given their important roles in many biological functions, it is likely that miRNAs will offer important points for therapeutic intervention or diagnostic analysis.

Characterizing the functions of biomolecules like miRNAs often involves introducing the molecules into cells or removing the molecules from cells and measuring the result. If introducing a miRNA into cells results in apoptosis, then the miRNA undoubtedly participates in an apoptotic pathway. Methods for introducing and removing miRNAs from cells have been described. Two recent publications describe antisense molecules that can be used to inhibit the activity of specific miRNAs (Meister et al., 2004; Hutvagner et al., 2004). Another publication describes the use of plasmids that are transcribed by endogenous RNA polymerases and yield specific miRNAs when transfected into cells (Zeng et al., 2002). These two reagent sets have been used to evaluate single miRNAs.

The present invention involves, in part, the inventors' discovery that several miRNAs are disregulated in certain types of breast cancer—those that have lost the expression of estrogen receptors (ER), progesterone receptors (PR), and HER2, also called human epidermal growth factor receptor 2 (HER2)—so called "triple-negative" breast cancers. Because these cancers do not respond to some types of cancer therapy, there is an imperative in their identification to as to avoid the cost and side effects of therapies which will do the patient little or no good, and focus more quickly on therapeutic options with a greater likelihood of success. These miRNAs are discussed below.

1. miR-193b

The sequence for miR-193b is provided as SEQ ID NO:1 (aacuggcccucaaagucccgcu), miRBase accession number MIMAT0002819. This molecule is predominantly expressed in muscle tissue, but also in cervix, placenta, prostate, testes and thymus. References describing this miRNA are Bentwich et al. (2005), and Sewer et al. (2005).

2. miR-34a

The sequence for miR-34a is provided as SEQ ID NO:2 (uggcagugucuuagcugguugu), miRBase accession number MIMAT0000255. This human miRNA was predicted by computational methods using conservation with mouse and *Fugu rubripes* sequences. Expression of the excised miR has been validated in zebrafish, and the ends mapped by cloning. Dostie et al. (2003) independently cloned this sequence in human but misnamed the sequence miR-172 (the sequence is unrelated to MIR172 from *Arabidopsis*). The sequence maps to human chromosome 1. Human miR-34a was previously named miR-34, but is renamed to clarify homology with the alternatively named mouse sequence (MI0000584). The mature sequence shown here represents the most commonly cloned form from large-scale cloning studies.

Other references describing this miRNA are Lim et al. (2003), Landgraf et al. (2007) and Lui et al. (2007).

3. miR-301a

The sequence for miR-301 is provided as SEQ ID NO:3 (cagugcaauaguauugucaaagc), miRBase accession number MIMAT0000688. References describing this miRNA are Griffiths-Jones et al. (2006), and Dogini et al. (2008).

4. miR-148a

The sequence for miR-148 is provided as SEQ ID NO:4 (ucagugcacuacagaacuuugu), miRBase accession number MIMAT0000243. miR-148a expression has been demonstrated in human (MI0000253), mouse (MI0000550), rat (MI0000616) and zebrafish (MI0002015). miR-148a has also been predicted in chicken (MI0001189). These predicted hairpin precursor sequence are related to those of miR-152, which has been expressed in mouse (MI0000174) and is predicted in human (MI0000462). Human miR-148 represses DNA methyltransferase 3b (Dnmt3b) gene expression through a region in its coding sequence.

References describing this miRNA are Lagos-Quintana et al. (2002), Kim et al. (2004), Chen et al. (2005) and Duursma et al. (2008).

5. miR-15b

The sequence for miR-15b is provided as SEQ ID NO:5 (uagcagcacaucaugguuuaca), miRBase accession number MIMAT0000417. miR-15b is down-regulated in multidrug resistant (MDR) gastric cancer, and overexpression of miR-15b sensitized SGC7901/VCR cells to anticancer drugs, whereas inhibition conferred SGC7901 cells with an MDR phenotype. The downregulation of miR-15b and miR-16 in SGC7901/VCR cells was concurrent with the upregulation of Bcl-2 protein. Lin et al. (2008). Other references describing this miRNA are Poy et al. (2004), Watanabe et al. (2006) and Landgraf et al. (2007).

6. miR-200c

The sequence for hsa-miR-200c is uaauacugccggguaaugaugga, miRBase accession number MI0000650. This molecule is expressed in cells with an epithelial phenotype and is lost when cancerous cells undergo epithelial to mesenchymal transition. References describing this miRNA are Hurteau et al. (2007) and Cochrane et al. (2009).

7. miR-29a

The sequence for hsaiR-29a is uagcaccaucugaaaucgguua, miRBase accession number MI0000087. This molecule is repressed by MYC and is upregulated in lung cancers. References describing this miRNA are Chang et al. (2008) and Fabbri et al. (2007).

8. miR-221/222

The sequence for hsamiR-221 is agcuacauugucugcugggguuc, miRBase accession number MI0000298. The sequence for has-miR-222 is agcuacaucuggcuacugggu, miRBase accession number MI0000299. Both miRNAs are transcribed on the same transcript. They both target the estrogen receptor and are associated with tamoxifen resistant breast cancers. References describing this miRNA are Miller et al. (2008) and Zhao et al. (2008).

B. Synthesis and Alternative Nucleic Acid Chemistries

Oligonucleotides like miRNAs are generally chemically synthesized using nucleoside phosphoramidites. A phosphoramidite is a derivative of natural or synthetic nucleoside with protection groups added to its reactive exocyclic amine and hydroxy groups. The naturally occurring nucleotides (nucleoside-3'-phosphates) are insufficiently reactive to afford the synthetic preparation of oligonucleotides. A dramatically more reactive (2-cyanoethyl) N,N-diisopropyl phosphoramidite group is therefore attached to the 3'-hydroxy group of a nucleoside to form nucleoside phosphoramidite. The protection groups prevent unwanted side reactions or facilitate the formation of the desired product during synthesis. The 5'-hydroxyl group is protected by DMT (dimethoxytrityl) group, the phosphite group by a diisopropylamino (iPr2N) group and a 2-cyanoethyl ($OCH_2CH_2CN$) group. The nucleic bases also have protecting groups on the exocyclic amine groups (benzoyl, acetyl, isobutyryl, or many other groups). In RNA synthesis, the 2' group is protected with a TBDMS (t-butyldimethylsilyl) group or with a TOM (t-butyldimethylsilyloxymethyl) group. With the completion of the synthesis process, all the protection groups are removed.

Whereas enzymes synthesize DNA in a 5' to 3' direction, chemical DNA synthesis is done backwards in a 3' to 5' reaction. Based on the desired nucleotide sequence of the product, the phosphoramidites of nucleosides A, C, G, and T are added sequentially to react with the growing chain in a repeating cycle until the sequence is complete. In each cycle, the product's 5'-hydroxy group is deprotected and a new base is added for extension. In solid-phase synthesis, the oligonucleotide being assembled is bound, via its 3'-terminal hydroxy group, to a solid support material on which all reactions take place. The 3' group of the first base is immobilized via a linker onto a solid support (most often, controlled pore glass particles or macroporouspolystyrene beads). This allows for easy addition and removal of reactants. In each cycle, several solutions containing reagents required for the elongation of the oligonucleotide chain by one nucleotide residue are sequentially pumped through the column from an attached reagent delivery system and removed by washing with an inert solvent.

Antagomirs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. In one embodiment, the antagomir includes a non-nucleotide moiety, e.g., a cholesterol moiety. The non-nucleotide moiety can be attached to the 3' or 5' end of the oligonucleotide agent.

A wide variety of well-known, alternative oligonucleotide chemistries may be used (see, e.g., U.S. Patent Publications 2007/0213292, 2008/0032945, 2007/0287831, etc.), particularly single-stranded complementary oligonucleotides comprising 2' methoxyethyl, 2'-fluoro, and morpholino bases (see e.g., Summerton and Weller, 1997). The oligonucleotide may include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMOE), 2'-O-dimethylaminopropyl (2'-O-DMAP), 2'-O-dimethylaminoethyloxyethyl (2'-O-DMAEOE), or 2'-O—N-methylacetamido (2'-O—NMA). Also contemplated are locked nucleic acid (LNA) and peptide nucleic acids (PNA).

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

Strand invasion by PNAs in cell-free systems is most potent at sequences that are partially single-stranded (Bentin and Nielsen, 1996; Zhang et al., 2000). Assembly of RNA polymerase and transcription factors into the pre-initiation complex on DNA induces the formation of a structure known as the open complex that contains several bases of single-stranded DNA (Holstege et al., 1997; Kahl et al., 2000). The exceptional ability of PNAs to recognize duplex DNA allows them to intercept the open complex of an actively transcribed gene without a requirement for preincubation. The open complex is formed during transcription of all genes and PNAs can be synthesized to target any transcription initiation site. Therefore, antigene PNAs that target an open complex at a promoter region within chromosomal DNA would have the potential to be general tools for controlling transcription initiation inside cells.

A locked nucleic acid (LNA), often referred to as inaccessible RNA, is a modified RNA nucleotide (Elmén et al., 2008). The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006). LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

Other oligonucleotide modifications can be made to produce oligonucleotides. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 05/115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3-) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an oligonucleotides by means of a pyrrolidine linker does not result in a significant loss of gene-silencing activity in cell culture. These studies demonstrates that cholesterol conjugation significantly improves in vivo pharmacological properties of oligonucleotides.

U.S. Patent Publication 2008/0015162, incorporated herein by reference, provides additional examples of nucleic acid analogs useful in the present invention. The following excerpts are derived from that document and are exemplary in nature only.

In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl.

In certain embodiments, the oligomeric compounds including, but no limited to short oligomers of the present invention, comprise one or more high affinity monomers provided that the oligomeric compound does not comprise a nucleotide comprising a 2'—$O(CH_2)_nH$, wherein n is one to six. In certain embodiments, the oligomeric compounds including, but no limited to short oligomers of the present invention, comprise one or more high affinity monomer provided that the oligomeric compound does not comprise a nucleotide comprising a 2'-$OCH_3$ or a 2'—$O(CH_2)_2OCH_3$. In certain embodiments, the oligomeric compounds comprise one or more high affinity monomers provided that the oligomeric compound does not comprise a α-L-methyleneoxy (4'-$CH_2$—O-2') BNA and/or a β-D-methyleneoxy (4'-$CH_2$—O-2') BNA.

Certain BNAs have been prepared and disclosed in the patent literature as well as in scientific literature (Singh et al., 1998; Koshkin et al., 1998; Wahlestedt et al., 2000; Kumar et al., 1998; WO 94/14226; WO 05/021570; Singh et al, 1998; examples of issued US patents and published applications that disclose BNAs include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-$CH_2$—O-2') linkage to form the bicyclic sugar moiety (reviewed in Elayadi et al., 2001; Braasch et al., 2001; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') BNA is used for the bicyclic moiety; in the case of an ethylene group in this position, the term ethyleneoxy (4'-CH$_2$CH$_2$—O-2') BNA is used (Singh et al., 1998; Morita et al., 2003). Methyleneoxy (4'-CH$_2$—O-2') BNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-CH$_2$—O-2') BNA that has also been discussed is α-L-methyleneoxy (4'-CH$_2$—O-2') BNA which has been shown to have superior stability against a 3'-exonuclease. The α-L-methyleneoxy (4'-CH$_2$—O-2') BNA's were incorporated into antisense gapmers and chimeras that showed potent antisense activity (Frieden et al., 2003).

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-CH$_2$—O-2') BNA, phosphorothioate-methyleneoxy (4'-CH$_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of oligomers for targets and/or increase nuclease resistance. A representative list of modified sugars includes, but is not limited to, bicyclic modified sugars (BNA's), including methyleneoxy (4'-CH$_2$—O-2') BNA and ethyleneoxy (4'-(CH$_2$)$_2$—O-2' bridge) BNA; substituted sugars, especially 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

The naturally-occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

C. Delivery

A variety of methods may be used to deliver oligonucleotides, including antagomirs and mimics, into a target cell. For cells in vitro embodiments, delivery can often be accomplished by direct injection into cells, and delivery can often be enhanced using hydrophobic or cationic carriers. Alternatively, the cells can be permeabilized with a permeabilization agent and then contacted with the oligonucleotide. The antagomir can be administered to the subject either as a naked oligonucleotide agent, in conjunction with a delivery reagent, or as a recombinant plasmid or viral vector which expresses the oligonucleotide agent.

For cells in situ, several applicable delivery methods are well-established, e.g., Elmen et al. (2008), Akinc et al. (2008); Esau et al. (2006), Krützfeldt et al. (2005). In particular, cationic lipids (see e.g., Hassani et al., 2004) and polymers such as polyethylenimine (see e.g., Urban-Klein, 2005) have been used to facilitate oligonucleotide delivery. Compositions consisting essentially of the oligomer (i.e., the oligomer in a carrier solution without any other active ingredients) can be directly injected into the host (see e.g., Tyler et al., 1999; McMahon et al., 2002). In vivo applications of duplex RNAs are reviewed in Paroo and Corey (2004).

When microinjection is not an option, delivery can be enhanced in some cases by using Lipofectamine™ (Invitrogen, Carlsbad, Calif.). PNA oligomers can be introduced into cells in vitro by complexing them with partially complementary DNA oligonucleotides and cationic lipid. The lipid promotes internalization of the DNA, while the PNA enters as cargo and is subsequently released. Peptides such as penetratin, transportan, Tat peptide, nuclear localization signal (NLS), and others, can be attached to the oligomer to promote cellular uptake (see e.g., Kaihatsu et al., 2003; Kaihatsu et al., 2004). Alternatively, the cells can be permeabilized with a permeabilization agent such as lysolecithin, and then contacted with the oligomer.

Alternatively, certain single-stranded oligonucleotide agents featured in the instant invention can be expressed within cells from eukaryotic promoters (e.g., Izant and Weintraub, 1985; McGarry and Lindquist, 1986; Scanlon et al., 1991; Kashani-Sabet et al., 1992; Propulic et al., 1992; Weerasinghe et al., 1991; Ojwang et al., 1992; Chen et al., 1992; Sarver et al., 1990; Thompson et al., 1995). Those skilled in the art realize that any nucleic acid can be expressed in eukaryotic cells from the appropriate DNA/RNA vector. The activity of such nucleic acids can be augmented by their release from the primary transcript by a enzymatic nucleic acid (PCT WO 93/23569; PCT WO 94/02595; Ohkawa et al., 1992; Taira et al., 1991; Ventura et al., 1993; Chowrira et al., 1994).

The recombinant vectors can be DNA plasmids or viral vectors. Oligonucleotide agent-expressing viral vectors can be constructed based on, but not limited to, adeno-associated virus, retrovirus, adenovirus, or alphavirus. In another embodiment, pol III based constructs are used to express nucleic acid molecules of the invention (see for example Morris et al., 2004; U.S. Pat. Nos. 5,902,880 and 6,146,886). The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the antagomir interacts with the target RNA (e.g., miRNA or pre-miRNA) and inhibits miRNA activity. In a particular embodiment, the antagomir forms a duplex with the target miRNA, which prevents the miRNA from binding to its target mRNA, which results in increased translation of the target mRNA. Delivery of oligonucleotide agent-expressing vectors can be systemic, such as by intravenous or intra-muscular administration, by administration to target cells ex-planted from a subject followed by reintroduction into the subject, or by any other means that would allow for introduction into the desired target cell (see Couture et al., 1996).

Methods for the delivery of nucleic acid molecules are also described in Akhtar et al. (1992), Akhtar (1995), Maurer et al. (1999), Hofland and Huang (1999), Lee et al. (2000), all of which are incorporated herein by reference. U.S. Pat. No. 6,395,713 and PCT WO 94/02595 and WO 00/53722 further describe general methods for delivery of nucleic acid molecules.

NUCLEIC ACID VECTORS

As mentioned above, miRNAs of the present invention may be delivered and produced via a recombinant vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found.

Vectors include plasmids, cosmids, viruses (bacteriophage, animal viruses, and plant viruses), and artificial chromosomes (e.g., YACs). One of skill in the art would be well equipped to construct a vector through standard recombinant techniques (Sambrook et al., 1989; Ausubel et al., 1996, both incorporated herein by reference). A vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

A. Expression Vectors or Expression Cassettes

The term "expression vector" refers to a vector containing a nucleic acid sequence coding for at least part of a gene product capable of being transcribed. In some cases, RNA molecules are then translated into a protein, polypeptide, or peptide. In other cases, such as with miRNAs, these sequences are not translated. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/ or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. The identity of tissue-specific promoters or elements, as well as assays to characterize their activity, is well known to those of skill in the art.

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

3. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

4. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

5. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACKT™ BACULOVIRUS EXPRESSION SYSTEM FROM CLONTECH®.

In addition to the disclosed expression systems of the invention, other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

C. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

DETECTION METHODS

In some embodiments, it may prove useful to assess the expression of miRNAs in a cell from a subject having or suspected of having breast cancer, including triple-negative breast cancer. Any method of detection known to one of skill in the art falls within the general scope of the present invention.

Nucleic acids can used be as probes or primers for embodiments involving nucleic acid hybridization. As such, they may be used to assess miRNA expression. Commerically available systems, such as Qiagen's miScript System™ are available for detection of miRNAs. Various aspects of nucleic acid detection as discussed below.

A. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In particular embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772 and U.S. Patent Publication 2008/0009439. The relevant portions of these and other references identified in this section of the Specification are incorporated herein by reference.

B. In Situ Hybridization

In situ hybridization (ISH) is a type of hybridization that uses a labeled complementary DNA or RNA strand (i.e., probe) to localize a specific DNA or RNA sequence in a portion or section of tissue (in situ), or, if the tissue is small enough (e.g. plant seeds, *Drosophila* embryos), in the entire tissue (whole mount ISH). This is distinct from immunohistochemistry, which localizes proteins in tissue sections. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

For hybridization histochemistry, sample cells and tissues are usually treated to fix the target transcripts in place and to increase access of the probe. As noted above, the probe is either a labeled complementary DNA or, now most commonly, a complementary RNA (riboprobe). The probe hybridizes to the target sequence at elevated temperature, and then the excess probe is washed away (after prior hydrolysis using RNase in the case of unhybridized, excess RNA probe). Solution parameters such as temperature, salt and/or detergent concentration can be manipulated to remove any nonidentical interactions (i.e., only exact sequence matches will remain bound). Then, the probe that was labeled with either radio-, fluorescent- or antigen-labeled bases (e.g., digoxigenin) is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

C. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to any sequence corresponding to a nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al. (1988), each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Reverse transcription (RT) of RNA to cDNA followed by quantitative PCR (RT-PCR) can be used to determine the relative concentrations of specific miRNA species isolated from a cell. By determining that the concentration of a specific mRNA species varies, it is shown that the gene encoding the specific mRNA species is differentially expressed. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

A second condition for an RT-PCR experiment is to determine the relative abundances of a particular mRNA species. Typically, relative concentrations of the amplifiable cDNAs are normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

RT-PCR can be performed as a relative quantitative RT-PCR with an internal standard in which the internal standard is an amplifiable cDNA fragment that is larger than the target cDNA fragment and in which the abundance of the mRNA encoding the internal standard is roughly 5-100-fold higher than the mRNA encoding the target. This assay measures relative abundance, not absolute abundance of the respective mRNA species.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Various nucleic acid detection methods known in the art are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Chip Technologies and Arrays

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of an miRNA with respect to diagnostic, as well as preventative and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

METHODS OF THERAPY

In some embodiments, the invention provides compositions and methods for the treatment of breast cancer, including triple-negative breast cancer. In one embodiment, the invention provides a method of treating cancer comprising administering to a patient an effective amount of a one or more miRNAs selected from miR-193b, miR-34a, miR-148a, miR-301 and miR-15b. This treatment may be further combined with additional cancer treatments. One of skill in the art will be aware of many treatments that may be combined with the methods of the present invention, some but not all of which are described below.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. miRNAs

One therapy approach is the provision, to a subject, of an miRNA. The miRNA is generally produced by an automated synthesizer (see above), although it may also be produced recombinantly. Formulations for delivery of the miRNA are selected based on the route of administration and purpose including, but not limited to, liposomal formulations and classic pharmaceutical preparations (discussed below).

Non-limiting examples of agents suitable for formulation with the miRNAs include P-glycoprotein inhibitors (such as PluronicP85), which can enhance entry of drugs into the CNS (Jolliet-Riant and Tillement, 1999), biodegradable polymers, such as poly(DL-lactide-coglycolide) microspheres for sustained release delivery. Other non-limiting examples of delivery strategies for miRNAs include material described in Boado et al. (1998), Tyler et al. (1999a; b); Pardridge et al. (1995); Boado (1995); Aldrian-Herrada et al. (1998).

The invention also features the use of a composition that includes surface-modified liposomes containing poly(ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., 1995; Ishiwata et al., 1995).

Such liposomes have been shown to accumulate selectively in tumors, presumably by extravasation and capture in the neovascularized target tissues (Lasic et al., 1995; Oku et al., 1995). The long-circulating liposomes enhance the pharmacokinetics and pharmacodynamics of DNA and RNA, particularly compared to conventional cationic liposomes which are known to accumulate in tissues of the MPS (Liu et al., 1995; PCT Publication No. WO 96/10391; PCT Publication No. WO 96/10390; PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

B. Genetic Delivery

The inventors also contemplate the use of expression constructs encoding miRNAs. The construction and structure of viral vectors is discussed above. Administration protocols would generally involve intratumoral, local or regional (to the tumor) administration, as well as systemic administration in appropriate clinical situations.

C. Formulations and Routes for Administration to Patients

In some embodiments, the invention provides a method of treating cancer comprising providing to a patient an effective amount of an miRNA. Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

"Treatment" and "treating" refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

A "disease" can be any pathological condition of a body part, an organ, or a system resulting from any cause, such as infection, genetic defect, and/or environmental stress.

"Prevention" and "preventing" are used according to their ordinary and plain meaning to mean "acting before" or such an act. In the context of a particular disease, those terms refer to administration or application of an agent, drug, or remedy to a subject or performance of a procedure or modality on a subject for the purpose of blocking the onset of a disease or health-related condition.

The subject can be a subject who is known or suspected of being free of a particular disease or health-related condition at the time the relevant preventive agent is administered. The subject, for example, can be a subject with no known disease or health-related condition (i.e., a healthy subject).

In additional embodiments of the invention, methods include identifying a patient in need of treatment. A patient may be identified, for example, based on taking a patient history or based on findings on clinical examination.

D. Cancer Combination Treatments

In some embodiments, the method further comprises treating a patient with cancer with a conventional cancer treatment. One goal of current cancer research is to find ways to improve the efficacy of chemo- and radiotherapy, such as by combining traditional therapies with other anti-cancer treatments. In the context of the present invention, it is contemplated that this treatment could be, but is not limited to, chemotherapeutic, radiation, a polypeptide inducer of apoptosis or other therapeutic intervention. It also is conceivable that more than one administration of the treatment will be desired.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Gene Therapy

In yet another embodiment, the secondary treatment is a gene therapy in which a therapeutic polynucleotide is administered before, after, or at the same time as an miRNA is administered. Delivery of an miRNA in conjunction with a vector encoding one of the following gene products may have a combined anti-hyperproliferative effect on target tissues. A variety of proteins are encompassed within the invention, some of which are described below.

a. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA or siRNA directed to a particular inducer of cellular proliferation is used to prevent expression of the inducer of cellular proliferation.

The proteins FMS and ErbA are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

b. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, mda-7, FHIT, p16 and C-CAM can be employed.

In addition to p53, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

c. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{XL}$, Bcl$_W$, Bcl$_S$, Mcl-1, A1, Bfl-1) or counteract Bcl-2 function and promote cell death (e.g., Bax, Bak, Bik, Bim, Bid, Bad, Harakiri).

6. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

E. Dosage

An miRNA can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antagomir (e.g., about 4.4×10$^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antagomir per kg of bodyweight. The unit dose, for example, can be administered by injection (e.g., intravenous or intramuscular, intrathecally, intratumorally or directly into an organ), inhalation, or a topical application.

Delivery of an miRNA directly to an organ can be at a dosage on the order of about 0.00001 mg to about 3 mg per organ, or particularly about 0.0001-0.001 mg per organ, about 0.03-3.0 mg per organ, about 0.1-3.0 mg per organ or about 0.3-3.0 mg per organ.

Significant modulation of target gene expression may be achieved using nanomolar/submicromolar or picomolar/subnanomolar concentrations of the oligonucleotide, and it is typical to use the lowest concentration possible to achieve the desired resultant increased synthesis, e.g., oligonucleotide concentrations in the 1-100 nM range are contemplated; more particularly, the concentration is in the 1-50 nM, 1-25 nM, 1-10 nM, or picomolar range. In particular embodiments, the contacting step is implemented by contacting the cell with a composition consisting essentially of the oligonucleotide.

In one embodiment, the unit dose is administered once a day, e.g., or less frequently less than or at about every 2, 4, 8 or 30 days. In another embodiment, the unit dose is not administered with a frequency (e.g., not a regular frequency). For example, the unit dose may be administered a single time. Because oligonucleotide agent can persist for several days after administering, in many instances, it is possible to administer the composition with a frequency of less than once per day, or, for some instances, only once for the entire therapeutic regimen.

An miRNA featured in the invention can be administered in a single dose or in multiple doses. Where the administration of the miRNA is by infusion, the infusion can be a single sustained dose or can be delivered by multiple infusions. Injection of the miRNA can be directly into the tissue at or near the site of interest. Multiple injections of can be made into the tissue at or near the site.

In a particular dosage regimen, the miRNA is injected at or near a disease site once a day for seven days, for example, into a tumor, a tumor bed, or tumor vasculature. Where a dosage regimen comprises multiple administrations, it is understood that the effective amount of the miRNA administered to the subject can include the total amount of miRNA administered over the entire dosage regimen. One skilled in the art will appreciate that the exact individual dosages may be adjusted somewhat depending on a variety of factors, including the specific antagomir being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. Variations in these dosage levels can be adjusted using standard empirical routines of optimization, which are well-known in the art. The precise therapeutically effective dosage levels and patterns can be determined by the attending physician in consideration of the above-identified factors.

In one embodiment, a subject is administered an initial dose, and one or more maintenance doses of an miRNA. The maintenance dose or doses are generally lower than the initial dose, e.g., one-half less of the initial dose. The maintenance doses are generally administered no more than once every 5, 10, or 30 days. Further, the treatment regimen may last for a period of time which will vary depending upon the nature of the particular disease, its severity and the overall condition of the patient. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or disorder, previous treatments, the general health and/or age of the subject, and other diseases present. It will also be appreciated that the effective dosage of the antagomir used for treatment may increase or decrease over the course of a particular treatment. Changes in dosage may result and become apparent from the results of diagnostic assays. For example, the subject can be monitored after administering an antagomir composition. Based on information from the monitoring, an additional amount of the antagomir composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$'s found to be effective in in vitro and in vivo animal models.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. MCF-7 and T47D breast cancer cells were grown in DMEM, 10% FBS, L-glutamine and penicillin/streptomycin. MDA-MB-231 cells were grown in media containing 5% FBS, HEPES, NEAA, L-glutamine, penicillin, streptomycin and insulin. BT-549 cells were grown in RPMI supplemented with 10% FBS and insulin. All cell lines were maintained at 37° C. in 5% $CO_2$. The identity of all the cell lines was confirmed by DNA profiling using the Identifiler Kit from Applied Biosystems (Foster City, Calif.).

miRNA microarray profiling. Total RNA was prepared using Trizol (Invitrogen) as per the manufacturer's instructions. The quality of the RNA was determined using the RNA 6000 Nano Assay in the Agilent 2100 Bioanalyzer. Labeling, hybridization to miRNA microarray slides and feature extraction was performed by Dharmacon (Lafayette, Colo.). The platform used is the Agilent miRNA microarray platform containing all miRNAs in the Sanger version 10 database. Each miRNA probe is spotted in 7 locations to allow for statistical analysis to be performed. Relative intensity data for the multiple probes for each miRNA was subjected to statistical filtering. Probes with p-values <=0.05 in at least 2 of the 8 slides were retained for further analysis. For the luminal versus triple-negative screen, the filtered array data was analysed and clustering was performed using GeneSpring GX 10 (Agilent Technologies). Data was filtered using a 1.5-fold change cutoff and a p-value of 0.05 (ANOVA, with Benjamini Hochberg FDR multiple testing correction). For the estradiol experiment, an error-weighted ANOVA was used with a Holm multiple test correction. Reported are the miRNAs with a p-value less that 0.05 and a 1.3-fold change.

Transfections. BT549 or MDA-MB-231 cells were plated one day prior to transfection. Lipofectamine 2000 (Invitrogen) was incubated with the miRNA mimics for miR-22, miR-221, miR-193b or miR-7 (Ambion) or scrambled negative control (Ambion) at a concentration of 50 nM incubated in serum free media for 20 minutes prior to addition to the cells. Cells were incubated with the transfection mix at 37° C.

for 4 h before replacement of FBS to 5%. Protein was harvested 72 h post-transfection using RIPA lysis buffer (1% NP40, 0.5% NaDeoxycholate, 0.1% SDS, 50 mM Tris, 150 mM NaCl, 5 mM EDTA) containing protease inhibitors.

Immunoblotting. Cell lysates (50 μg) in SDS sample buffer were denatured and separated on 8% SDS PAGE gels and transferred to PVDF membranes. The membranes were blocked in 5% milk in TBS-T, and then probed overnight at 4° C. Primary antibodies were diluted in 5% milk in TBS-T. The primary antibodies used were: ERα (clone AER611 from NeoMarkers), FASN (rabbit polyclonal (H-300) from Santa Cruz Biotechnology), PARP (rabbit polyclonal from Cell Signaling Technology), β-actin (monoclonal AC-74 from Sigma), β-tubulin (clone B-5-1-2 from Sigma) EGFR (rabbit polyclonal from Cell Signaling Technology), IGF1Rβ (rabbit polyclonal (C-20) from Santa Cruz Biotechnology), IRS-1 (from Doug Yee's laboratory), IRS-2 (rabbit polyclonal (H-205) from Santa Cruz Biotechnology), ERK1/2 (MAPK), phosphor-specific and total (rabbit polyclonals from Cell Signaling Technology). After incubation with appropriate HRP-conjugated secondary antibody, results were detected using Western Lightning Chemiluminescence Reagent Plus (Perkin Elmer).

Luciferase Assays. A 360 bp fragment of the 3' untranslated region of ESR1 containing the putative binding sites for miR-203, miR-221 and miR-22 was amplified by PCR from HeLa genomic DNA (NEB) using the following primers: ESR1-1 F 5'-CCACTAGTGTCATTTATGCCT-3' (SEQ ID NO: 6) and ESR1-1 R 5'-CTCAAGCTTCCTTCCACTGT-3' (SEQ ID NO: 7). A 680 bp fragment containing the putative binding sites for miR-130/301, miR-148/152, miR-19 and miR-26 was amplified using the following primers: ESR1-2 F 5'-CCACTAGTCTCAACTGGAGCA-3' (SEQ ID NO: 8) and ESR1-2 R 5'-CTCAAGCTTACAGGTGCTCG-3' (SEQ ID NO: 9). MCF7 cells (20,000 cells/well) in a 96-well plate were transfected with the 100 nM of the negative control, 50 nM each of the miR-22, miR-221 or both as described above. After 24 h, the firefly reporter plasmid (0.196 μg) and a *renilla* luciferase normalization plasmid (0.004 μg/pRL-SV40, Promega) were transfected in using Lipofectamine 2000. Cells were collected 48 hours later for assay using the Dual Luciferase Reporter assay system (Promega).

Hormone Treatments. MCF7 cells were grown in phenol red-free media containing charcoal stripped serum for 24 hours prior to hormone treatments. The cells were treated with ethanol, 10 nM estradiol or a combination of 10 nM estradiol and 1 mM ICI 182,780 (ICI, Tocris Bioscience) for 6 h, 24 h or 48 h, as indicated, before harvesting RNA using Trizol (Invitrogen) as per the manufacturer's instructions.

Real Time RT-PCR. Poly A tailing and reverse transcription was performed using the NCode miRNA qRT-PCR kit (Invitrogen) as per manufacturer's instructions. SYBR green real time RT-PCR was performed using the Universal Forward Primer (Invitrogen) and miRNA specific primers. The specific primers used were: miR-193b 5'-CGGGGTTTTGAGGGCGAGATGA-3' (SEQ ID NO: 10); miR-19b 5'-AGTTTTGCAGGTTTGCATCCAGC-3' (SEQ ID NO: 11); miR-20a 5'-ACTGCATTATGAGCACT-TAAAG-3' (SEQ ID NO: 12); miR-106a 5'-AAAAGTGCT-TACAGTGCAGGTAG-3' (SEQ ID NO: 13); and miR-92b* 5'-AGGGACGGGACGCGGTGCAGTG-3' (SEQ ID NO: 14). Reported values are the means and standard errors of 3 biological replicates.

For miR-22, miR-221 and miR-7, taqman real time PCR was performed. Prior to generating cDNA, mRNA was treated with DNase1 (Invitrogen) for 15 min at room temperature. RNA was reverse transcribed into cDNA in a reaction containing reaction buffer, 10 mM DTT, 1 mM dNTPs, RNAse inhibitor (Promega), random hexamers (250 ng) and 200 U of MMUV-RT (ABI). The reaction proceeded at 25° C. for 10 min, then at 37° C. for 1 h. For normalization, real time RT-PCR was performed on the cDNA using ribosomal RNA primers and probe (ABI). TaqMan mRNA Reverse Transcription kit was used to generate cDNA for real time RT-PCR reaction in conjunction with a miR-22, miR-221 or miR-7 specific primers and probe (ABI). Reported values are the means and standard errors of three biological replicates.

The relative mRNA or miRNA levels were calculated using the comparative Ct method (ΔΔCt). Briefly, the Ct (cycle threshold) values for the rRNA were subtracted from Ct values of the target gene to achieve the ΔCt value. The $2^{-\Delta Ct}$ was calculated for each sample and then each of the values was then divided by a control sample to achieve the relative miRNA levels (ΔΔCt).

Example 2

Results

Figure 1B:
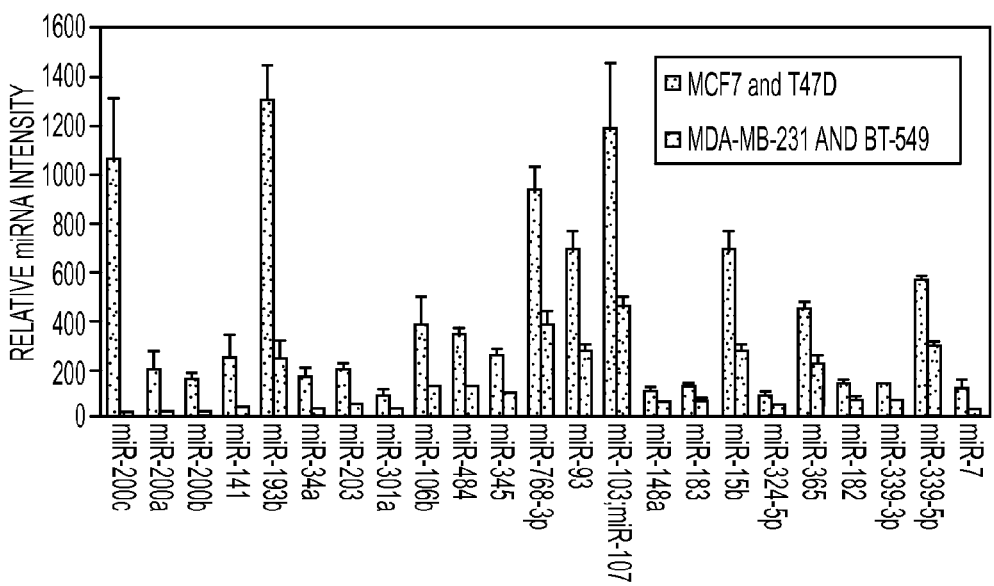
Figure 1C:
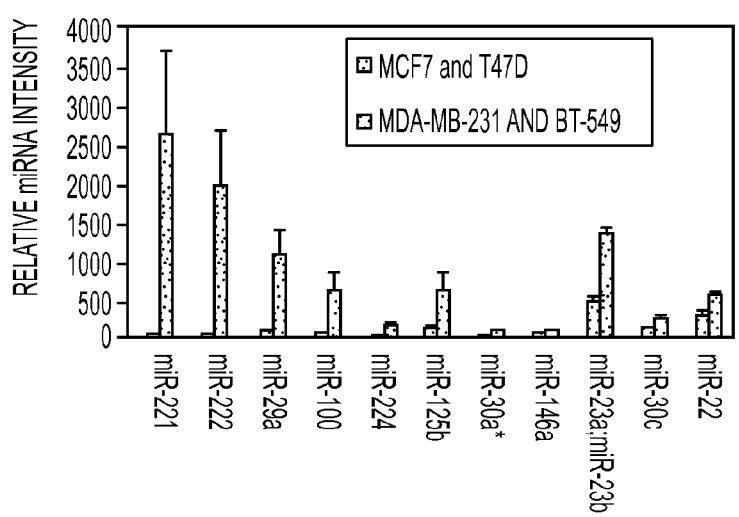

MiRNA microarray profiling of triple-negative versus luminal cell lines. MiRNA microarray profiling was performed on two well-differentiated, ESR1/progesterone receptor (PR)-positive breast cancer cell lines (MCF7 and T47D) as compared to two poorly-differentiated, triple-negative breast cancer cell lines (BT549 and MDA-MB-231). MiRNAs that were 1.5-fold or more differentially regulated between the two subtypes of breast cancer with a p-value less than 0.05 are depicted in a heatmap (FIG. 1A) and graphical representations of the miRNAs upregulated and downregulated in TN versus luminal are shown (FIG. 1B and FIG. 1C, respectively). The inventors find that there are more miRNAs decreased in the TN cells compared to the luminal cells. This is consistent with previous studies showing global downregulation of miRNAs in less differentiated cancers (Kumar et al., 2007; Lu et al., 2005).

The miRNAs that are most highly overexpressed in the TN versus luminal are miR-221 and miR-222 with a-fold difference of 90 and 68, respectively. These miRNAs belong to the same family, share a common seed sequence and therefore will target the majority of the same transcripts. Since these miRNAs reside close to each other on the X chromosome, they are transcribed on the same transcript and are therefore share the same expression patterns. miR-22 is also higher in the TN cells compared to the luminal cells, however the difference is only 2-fold. miR-221/222 and miR-22 have all previously been shown to directly target ESR1 (Miller et al., 2008; Pandey and Picard, 2009; Zhao et al., 2008).

Figure 3A:
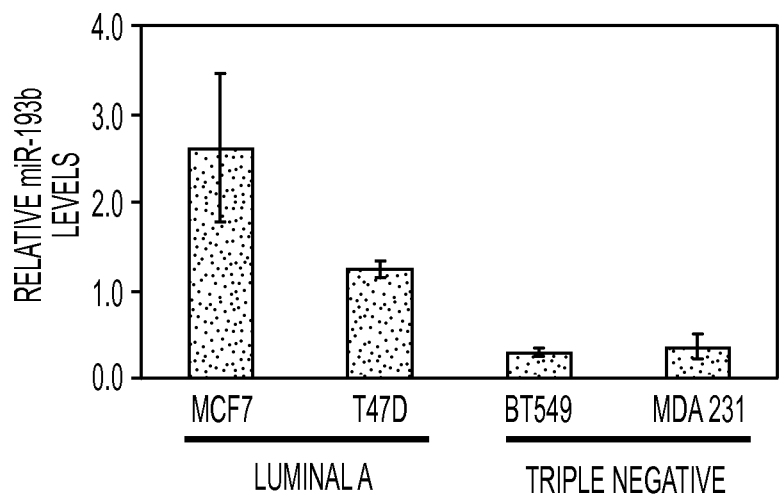
FIGS. 3A-C—MiR-193b targets FASN and induces apoptosis.
Figure 3B:
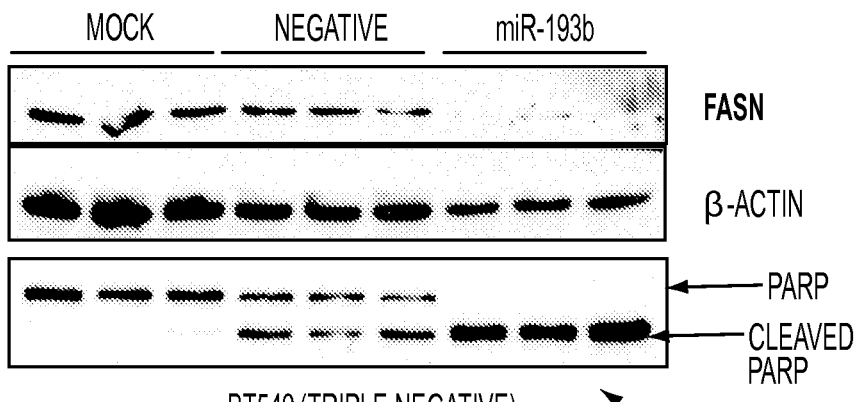
Figure 3C:
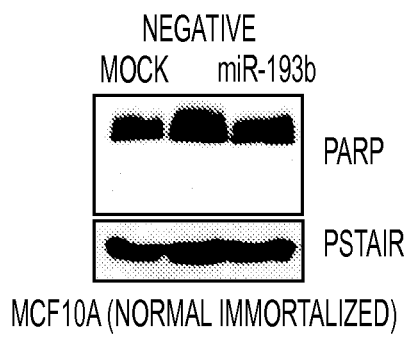
Figure 4A:
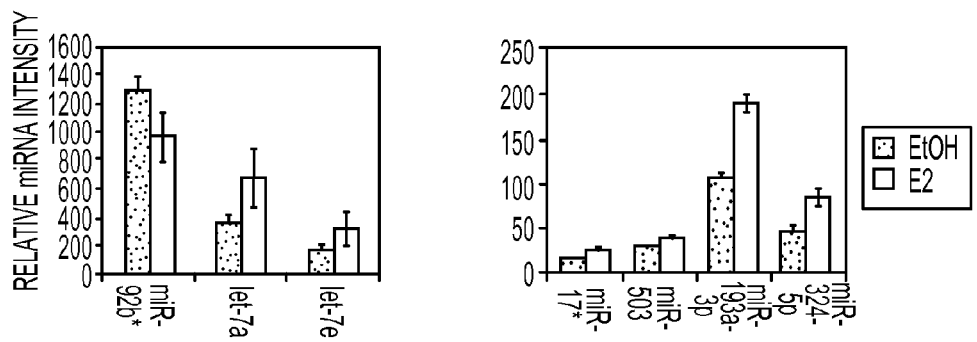
FIGS. 4A-C—miRNAs regulated by estrogen. miRNA microarray analysis of miRNAs differentially regulated by 10 nM estradiol at 6 h (FIG. 4A) or 24 h (FIG. 4B) versus the ethanol vehicle controls in MCF7 cells. Error bars represent the range from biological duplicate samples.
Figure 4B:
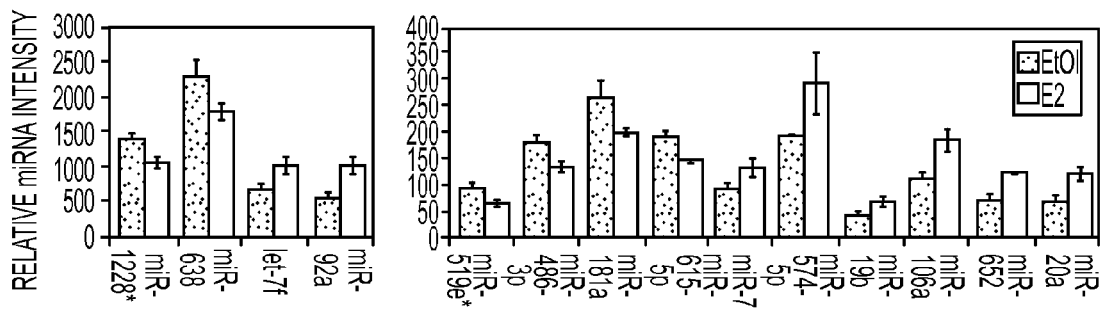
Figure 4C:
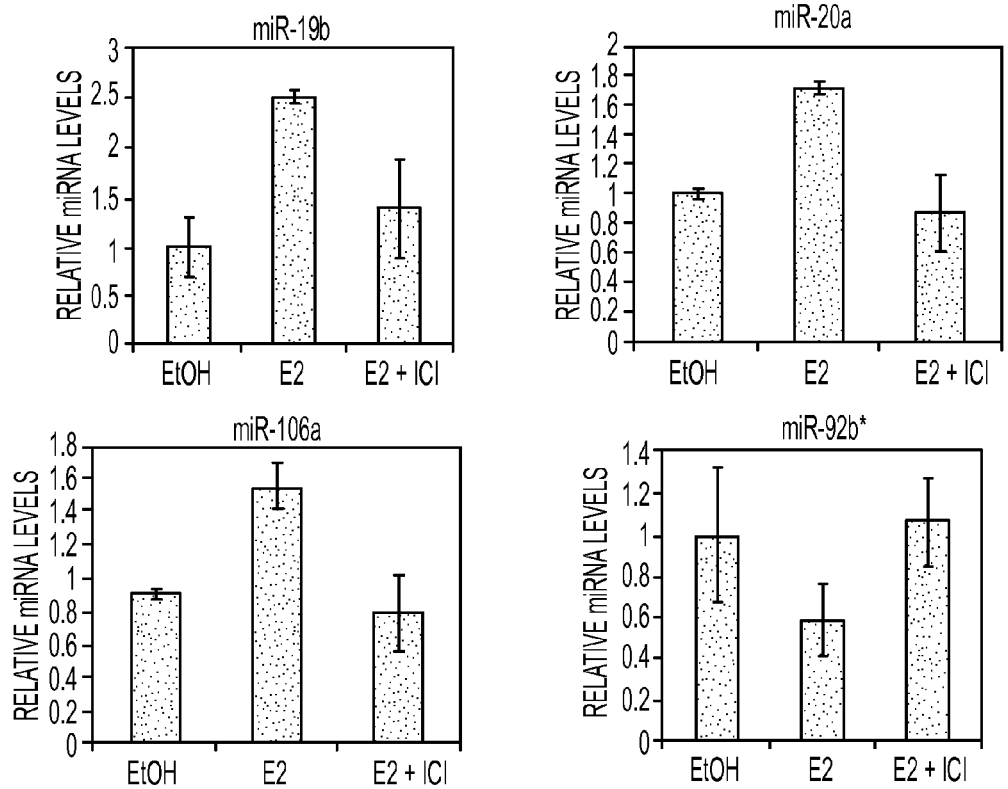
Figure 6:
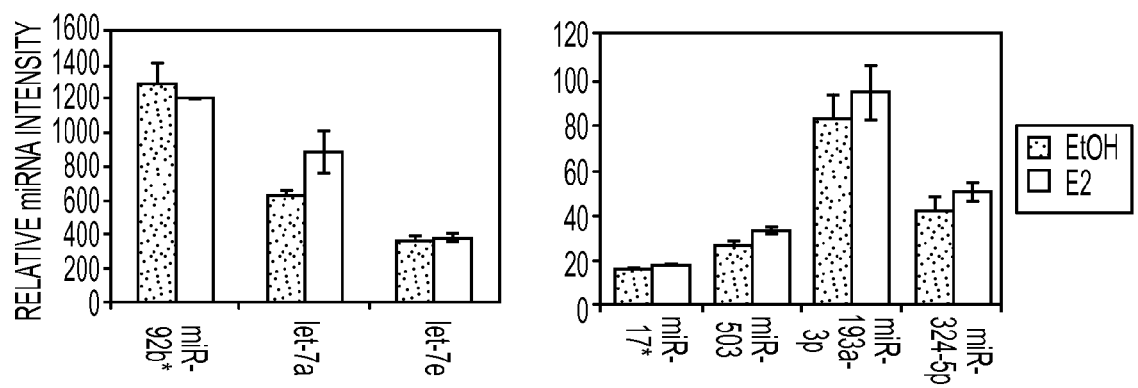
FIG. 6—Expression of miRNAs that were found to be differentially expressed at 6 h of estradiol treatment have similar expression trends at 24 h. MCF7 cells were treated with estradiol (E2) or a vehicle control (EtOH) for 6 h or 24 h and miRNA microarray profiling was performed. The expression levels at 24 h of estradiol treatment of the miRNAs that were found to be 1.3-fold or more differentially expressed at 6 h.
Figure 7:
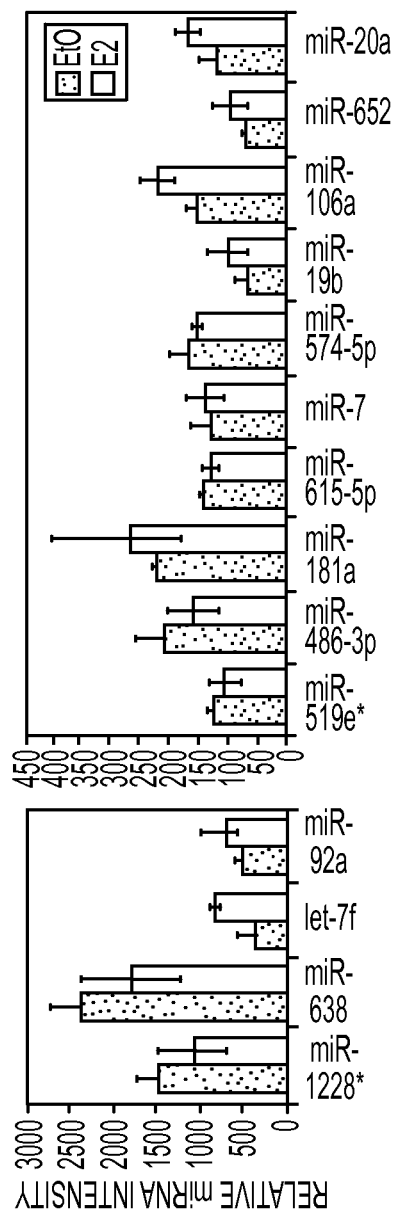
FIG. 7—Expression of miRNAs that were found to be differentially expressed at 24 h of estradiol treatment have similar expression trends at 6 h. MCF7 cells were treated with estradiol (E2) or a vehicle control (EtOH) for 6 h or 24 h and miRNA microarray profiling was performed. The expression levels at 6 h of estradiol treatment of the miRNAs that were found to be 1.3-fold or more differentially expressed at 24 h.

All four of the most highly overexpressed miRNAs in the luminal versus the TN cells (miR-200c, -200a, -200b and -141) belong to the miR-200 family, with miR-200c being 53-fold higher in the luminal cells. The inventors' laboratory and others have previously shown this family to control epithelial identity by repressing ZEB1 and ZEB2, as well as other mesenchymal genes (Hurteau et al., 2007; Park et al., 2008; Korpal et al., 2008; Cochrane et al., 2009; Paterson et al., 2008; Gregory et al., 2008). The loss of miR-200c in these triple-negative cells that have undergone EMT is consistent with previous observations (Cochrane et al., 2009), as members of the miR-200c family are usually only expressed in cells with an epithelial-like phenotype. After the miR-200 family, the miRNA that is most highly overexpressed in the luminal cells is miR-193b, which has a 6-fold difference compared to TN. miR-7 is also increased in luminal cells, 2.9-fold compared to TN.

miR-221 and miR-22 work cooperatively to downregulate ESR1. Real time rt-PCR was performed to validate the microarray data and confirm that miR-22 and miR-221 are higher in BT549 and MDA-MB-231 cells compared to MCF7 and T47D cells (FIG. 2A and FIG. 2B). Each of these miRNAs have been previously reported to target ESR1 (Zhao et al., 2008; Miller et al., 2008; Pandey and Picard, 2009). Mapping of the miRNAs predicted to target ESR1 3' UTR using Miranda, PicTar and Targetscan target prediction databases shows that the miR-221/222 and miR-22 target sites reside in close proximity (FIG. 2C). miRNAs can work cooperatively to downregulate a target when their target sites are near to each other (Saetrom et al., 2007; Chen et al., 2009). While each miRNA when added alone to ESR1-positive MCF7 cells causes a marked decrease in ESR1 protein, there is an additive effect when both miRNAs are combined (FIG. 2D). To demonstrate direct targeting of the miRNAs to the 3'UTR of the ESR1 transcript, the inventors performed luciferase assay. Two regions of the ESR1 3'UTR were cloned into the region 3' of the luciferase gene on a reporter vector. The region denoted ESR1-1 contains the miR-22 and miR-221 target sites. ESR1-2 is not predicted to be targeted by either miRNA and serves as a negative control. As another negative control, the inventors used the empty vector luciferase reported which will have constitutive luciferase expression. These vectors were transfected into MCF7 cells in combination with a scrambled negative control, the miR-22 or miR-221 mimics alone or in combination (FIG. 2E). The inventors observed an 18.8% decrease in luciferase activity in the cells transfected with ESR1-1 and the miR-22 mimic compared to the scrambled negative control. With the miR-221 mimic, there is a 13.7% decrease in luciferase activity versus the negative control. When both mimics are combined, they observe a 32.7% decrease in luciferase activity, demonstrating an additive effect when the miRNAs are combined.

miR-193 exerts control over lipid biosynthesis. The miRNA microarray data has shown that miR-193b had the second most sizeable decrease in expression between luminal and TN cells after the miR-200 family. To validate the microarray data, the inventors performed rt-PCR on luminal and triple-negative cell lines for miR-193b and confirm that it is indeed more highly expressed in the luminal cell lines (FIG. 3A). Targetscan target prediction software was used to query the putative targets of miR-193. The predicted targets included fatty acid synthase (FASN). Aggressive breast cancer cells exhibit altered metabolism, including an increased reliance on the de novo fatty acid synthesis pathway, even when there are ample dietary lipids available (Young and Anderson, 2008; Menendez and Lupu, 2004). One of the key enzymes in the de novo fatty acid synthesis pathway is FASN. Breast cancers that overexpress FASN have a poor prognosis (Alo et al., 1999; Alo et al., 1996). The inventors demonstrated that introduction of a miR-193b mimic into TN cells results in an almost complete repression of FASN protein (FIG. 3B). The inventors further demonstrated that there is a resultant increase in apoptosis in the miR-193b mimic treated cells, as seen by the appearance of cleaved PARP (FIG. 3B). There is some toxicity of the scrambled negative control which results in some PARP cleavage, however it is much less than the complete PARP cleavage observed with the miR-193b mimic. However, no apoptosis is observed when miR-193b is transfected into MCF10A (normal immortalized) cells (FIG. 3C).

miRNA microarray profiling of estrogen treated cells. To determine which miRNAs are regulated by ESR1, the inventors performed miRNA microarray profiling of MCF7 cells treated for 6 h or 24 h with ethanol vehicle control or 10 nM estradiol. In general, there were more miRNAs affected after 24 h of estradiol treatment. At 6 h, the inventors observed one miRNA decreasing, and six miRNAs increasing with estradiol (FIG. 4A). In general, the miRNAs seen changing at 6 h, show the same trend at 24 h; however, they do not reach statistical significance (FIG. 6). The inventors observed six miRNAs decreasing and eight miRNAs increasing at 24 h of estradiol treatment (FIG. 4B). The majority of these miRNAs have the same trend of expression at 6 h of treatment (FIG. 7). To validate these results, the inventors performed real time rt-PCR for several of the miRNAs (FIG. 4C) on cells treated with a vehicle control, estradiol or estradiol and ICI (an estrogen receptor antagonist). For each miRNA, the real time rt-PCR was performed for 24 and 48 h of treatment and shown is the time point with the most dramatic results. miR-19b, miR-20a and miR-106a are all increased with estradiol treatment at 48 h, and this effect is abrogated by ICI. miR-92b* is decreased with estradiol treatment at 24 h, and this effect is reversed by ICI.

Figure 5A:
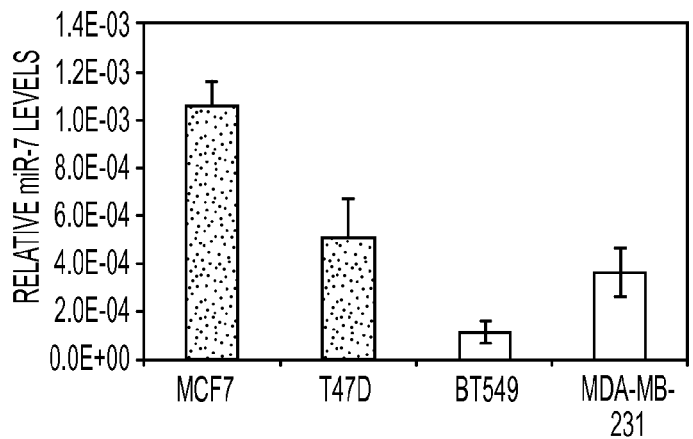
FIGS. 5A-C—miR-7 targets growth factor receptors and downstream signaling molecules.
Figure 5B:
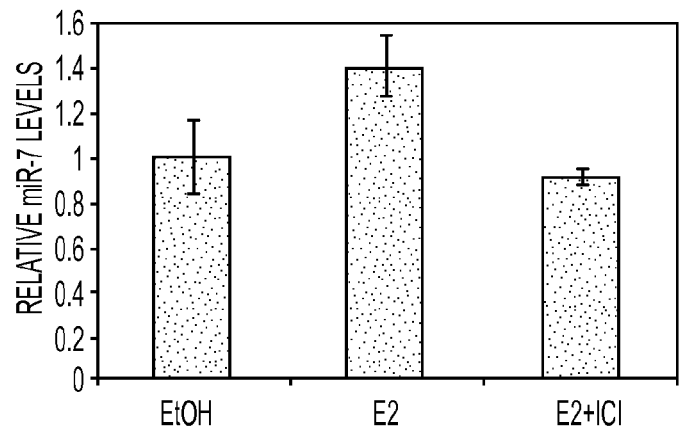
Figure 5C:
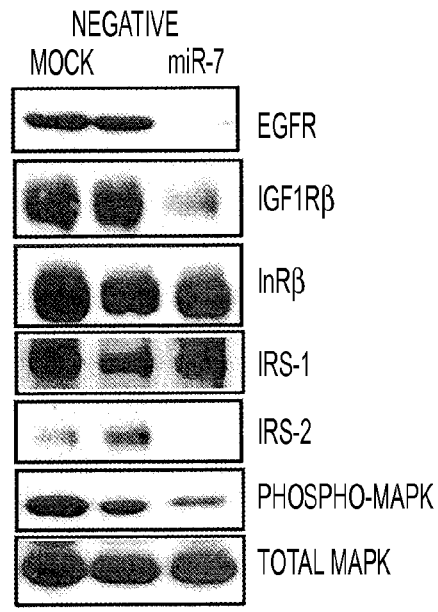

MiR-7 targets growth factor receptors that are overexpressed in triple-negative breast cancers. Only two miRNAs were found to be significantly altered in both miRNA microarray screens, miR-7 and miR-324-5p. In both cases, the miRNAs are increased with estradiol treatment and are decreased in cells lacking ESR1. The inventors confirmed the miRNA microarray experiments for miR-7 using real time rt-PCR and showed that it is decreased in the TN cell lines (FIG. 5A) and increased with estradiol treatment (FIG. 5B). miR-7 is predicted bioinformatically to target the epidermal growth factor receptor (EGFR), insulin-like growth factor 1 receptor (IGF1R), insulin receptor substrates 1 and 2 (IRS-1, IRS-2). EGFR and IGF1R are growth factor receptors that are often overexpressed in triple-negative breast cancers and contribute to increased aggressiveness of these cells (Adelaide et al., 2007; Klinakis et al., 2009; Law et al., 2008; Lerma et al., 2007; Meche et al., 2009). The IRS proteins are signaling intermediates in the insulin receptor and IGF1R pathways. The inventors show that addition of a miR-7 mimic to TN cells causes a decrease in both EGFR and IGF1Rβ receptors (FIGS. 5A-B). The inventors did not observe any effect on the insulin receptor with miR-7 treatment. There was also an almost complete knockdown of IRS-2 with the addition of the miR-7 mimic. Even though miR-7 is predicted bioinformatically to also target IRS-1, the inventors did not observe any decrease in its protein levels. Finally, the inventors observed a decrease in phosphorylation of ERK1/2 (MAPK), a downstream signaling molecule, but no effect on total MAPK levels.

Example 3

Discussion

Breast cancers are classified into several subtypes, each with having unique characteristics which classify their aggressiveness and treatment options (Morris and Carey, 2007; Kaklamani and Gradishar, 2006). The most differentiated subtype of breast cancer is the luminal A cancers. These retain their hormone receptors (ESR1 and PR) and can therefore be targeted with endocrine therapy (de Ronde et al., 2009). Luminal B cancers retain their hormone receptors, but also overexpress the cell surface receptor HER2/neu. These cancers are sensitive to herceptin therapy, an antibody that recognizes HER2 and prevents signaling through it. Triple-negative/basal breast cancers are the most poorly-differentiated subtype of breast cancer. They have lost their hormone receptors and therefore can not be treated with antiestrogens.

They also do not overexpress HER2 and do not respond to herceptin therapy. TN cancers represent the most aggressive of the breast cancer subtypes with the poorest prognosis since treatment options are limited (Rakha and Ellis, 2009; Stockmans et al., 2008). TN cancers tend to have altered expression of other proteins which contributes to their aggressive nature, such as overexpression of growth factor receptors such as IGF1R and EGFR which act mitogenically to cause uncontrolled proliferation (Adelaide et al., 2007; Klinakis et al., 2009; Meche et al., 2009). Furthermore, TN cancers often have altered metabolism which includes an increase the de novo fatty acid synthesis pathway.

In this report, the inventors have profiled cell lines that represent the two extremes of the breast cancer subtypes: the well-differentiated luminal A cell lines, and poorly-differentiated triple-negative cell lines. One of the advantages to using cell lines compared to human tumor samples is that they represent a relatively pure population. Many miRNAs have been previously shown to be expressed only in a specific cell type. For example miR-200c is only expressed in cells with an epithelial phenotype and not in mesenchymal cells (Cochrane et al., 2009). Tumors will have several different cell types, including both epithelium and stroma, and profiling of these tumors may not be able to distinguish miRNAs that are restricted to one cell type. Previous miRNA profiling using tumor samples of different subtypes has been performed. Several of the miRNAs that were differentially expressed in luminal versus TN cell lines in our data, were included in a signature of miRNAs that could distinguish the different subtypes of breast cancer. These include miR-15b, miR-200a, miR-7 and miR-100 (Blenkiron et al., 2007). Notably, the miRNAs that the inventors found with the highest-fold differences such as miR-221/222, miR-200c and miR-193 were not found to be differentially expressed when the tumors were profiled. Since the expression of these may be confined to a particular cell type, changes between the different breast cancer subtypes may not be distinguishable when whole tumors are used as they contain a mixture of many different cell types. Sempere et al. (2007) have performed miRNA profiling on both breast cancer tumors and cell lines. They found that miR-221 and miR-222 to have high expression in the basal cell lines and tumors compared to luminal cell lines and tumors, which is consistent with our findings. Interestingly, they found the miR-200 family to be lost in the basal cell lines compared to the luminal one, similar to what the inventors observe, but the opposite to be true in the tumor samples where the miR-200 family is higher in the basal tumors. Again, the inventors propose that this discrepancy is due to having a mixed cell population when profiling tumors.

The inventors' profiling experiment shows that there are more miRNAs that are decreased in the TN cell lines as compared to the luminal cell lines. It has been often observed that cancer cells in general exhibit more miRNA losses than gains (Kumar et al., 2007; Lu et al., 2005). This is partially due to miRNAs mapping to fragile sites that are often lost in cancers (Zhang et al., 2008), as well as an impairment in miRNA processing (Kumar et al., 2007). The inventors performed a second miRNA microarray profiling experiment to determine which miRNAs are regulated by ESR1. Since ESR1 signaling is important in breast cancer, miRNAs that are regulated by estradiol may contribute to cancer progression.

The inventors' miRNA microarray profiling of the luminal and triple-negative cell lines demonstrates that many miRNAs are differentially expressed in the two breast cancer subtypes. But more importantly, the inventors demonstrate that several of these miRNAs have functional significance by targeting mRNAs that define these two subtypes. MiR-22 and miR-221/222 are known to target ESR1 (Pandey and Picard, 2009; Zhao et al., 2008), which is one of the most important molecular markers of luminal cancers. Loss of ESR1 expression in TN cancers can be explained in some cancers by an overexpression of these two miRNAs. The inventors show here that these miRNAs work in concert to decrease ESR1 protein levels more than either miRNA alone.

Cancers exhibit altered metabolism which includes increased glucose uptake, increased lactate production and a reliance on de novo fatty acid synthesis (Young and Anderson, 2008). For reasons that remain unclear, cancer cells will use the de novo fatty acid synthesis pathway even when there is an excess of dietary lipids available (Mashima et al., 2009). FASN, which is one of the main enzymes in the de novo fatty acid synthesis pathway, is often overexpressed in cancers and is a marker for poor prognosis in breast cancer (Jensen et al., 2008; Vazquez-Martin et al., 2008). Since cancer cells have a high rate of proliferation, they have increased requirements of lipids to generate membranes. This partially explains the need for increased lipid synthesis, however FASN appears to play further roles in cancer cell survival De Schrijver et al., 2003; Swinnen et al., 2003). Pharmacological inhibition of FASN is an avenue actively being studied as a potential therapeutic for breast cancer (Puig et al., 2008; Menendez et al., 2005; Alli et al., 2005). The inventors' miRNA microarray screening and subsequent real time rt-PCR validation show that miR-193, which is predicted to target FASN, is decreased in the TN cells compared to luminal. They demonstrate here that miR-193b is able to target FASN and almost completely knock down protein expression. The knockdown of FASN is accompanied with an appearance of PARP cleavage product indicating apoptosis is occurring. Therefore, restoration of miR-193 to aggressive TN cancer cells that rely on de novo fatty acid synthesis may have therapeutic potential.

Rather surprisingly, there were only two miRNAs in common between the two screens. Since luminal cells retain ESR1 while TN cells have lost it, the inventors expected many of the estradiol-regulated miRNAs to also have an inverse correlation with ESR1 status. Microarray profiling may not be sensitive enough to detect some of the changes in miRNA expression. Also, there may be ligand independent regulation of miRNAs by ESR1.

One of the miRNAs that appeared in both microarray screens was miR-7, which has previously shown to target EGFR and cause a decrease in proliferation (Webster et al., 2009; Li and Carthew, 2005). The inventors show here that it also targets IGF1R and IRS-2. EGFR and IGF1R are often overexpressed in TN breast cancers and contribute to an aggressive phenotype. IRS-2 is a signaling intermediate in the IGF1R pathway and therefore miR-7 can more effectively abrogate this signaling pathway by targeting two of its key members Inhibitors specific for either EGFR or IGF1R show promise as treatments for TN breast cancers (Halterman, 2008; Mukohara et al., 2009). The inventors' data suggest that re-introduction of miR-7 into TN cells may offer an advantage over these agents because it targets both pathways simultaneously.

The data presented here shows that the miRNAs that are differentially expressed in luminal versus TN breast cancers and others are regulated by estrogen. The inventors find that these miRNAs target specific transcripts such as ESR1, FASN, IGF1R and EGFR which are important in defining the molecular phenotype of breast cancer.

All of the methods and apparatus disclosed and claimed herein can be made and executed without undue experimentation in light of the present disclosure. While the compositions and methods of this invention have been described in terms of particular embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,195
U.S. Pat. No. 4,683,202
U.S. Pat. No. 4,800,159
U.S. Pat. No. 4,879,236
U.S. Pat. No. 4,883,750
U.S. Pat. No. 4,981,957
U.S. Pat. No. 5,118,800
U.S. Pat. No. 5,143,854
U.S. Pat. No. 5,202,231
U.S. Pat. No. 5,242,974
U.S. Pat. No. 5,279,721
U.S. Pat. No. 5,288,644
U.S. Pat. No. 5,319,080
U.S. Pat. No. 5,324,633
U.S. Pat. No. 5,359,044
U.S. Pat. No. 5,384,261
U.S. Pat. No. 5,393,878
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,466,786
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,514,785
U.S. Pat. No. 5,519,134
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,567,811
U.S. Pat. No. 5,571,639
U.S. Pat. No. 5,576,427
U.S. Pat. No. 5,580,726
U.S. Pat. No. 5,580,732
U.S. Pat. No. 5,591,722
U.S. Pat. No. 5,593,839
U.S. Pat. No. 5,597,909
U.S. Pat. No. 5,599,672
U.S. Pat. No. 5,599,695
U.S. Pat. No. 5,610,300
U.S. Pat. No. 5,610,287
U.S. Pat. No. 5,624,711
U.S. Pat. No. 5,627,053
U.S. Pat. No. 5,631,134
U.S. Pat. No. 5,639,603
U.S. Pat. No. 5,639,873
U.S. Pat. No. 5,646,265
U.S. Pat. No. 5,654,413
U.S. Pat. No. 5,658,734
U.S. Pat. No. 5,658,873
U.S. Pat. No. 5,661,028
U.S. Pat. No. 5,665,547
U.S. Pat. No. 5,667,972
U.S. Pat. No. 5,670,633
U.S. Pat. No. 5,695,940
U.S. Pat. No. 5,700,637
U.S. Pat. No. 5,700,920
U.S. Pat. No. 5,739,169
U.S. Pat. No. 5,744,305
U.S. Pat. No. 5,792,747
U.S. Pat. No. 5,800,992
U.S. Pat. No. 5,801,005
U.S. Pat. No. 5,807,522
U.S. Pat. No. 5,824,311
U.S. Pat. No. 5,830,645
U.S. Pat. No. 5,830,880
U.S. Pat. No. 5,837,196
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,847,219
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,871,928
U.S. Pat. No. 5,871,986
U.S. Pat. No. 5,876,932

U.S. Pat. No. 5,882,864
U.S. Pat. No. 5,900,481
U.S. Pat. No. 5,902,880
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,004,755
U.S. Pat. No. 6,087,102
U.S. Pat. No. 6,146,886
U.S. Pat. No. 6,268,490
U.S. Pat. No. 6,368,799
U.S. Pat. No. 6,383,749
U.S. Pat. No. 6,395,713
U.S. Pat. No. 6,525,191
U.S. Pat. No. 6,531,584
U.S. Pat. No. 6,600,032
U.S. Pat. No. 6,617,112
U.S. Pat. No. 6,638,717
U.S. Pat. No. 6,670,461
U.S. Pat. No. 6,720,138
U.S. Pat. No. 6,770,748
U.S. Pat. No. 6,794,499
U.S. Pat. No. 7,034,133
U.S. Pat. No. 7,053,207
U.S. Patent Publn. 2003/0082807
U.S. Patent Publn. 2003/0207841
U.S. Patent Publn. 2004/0014959
U.S. Patent Publn. 2004/0143114
U.S. Patent Publn. 2004/0171570
U.S. Patent Publn. 2004/0219565
U.S. Patent Publn. 2007/0213292
U.S. Patent Publn. 2007/0287831
U.S. Patent Publn. 2008/0009439
U.S. Patent Publn. 2008/0015162
U.S. Patent Publn. 2008/0032945
Adelaide et al., *Cancer Res.*, 67:11565-11575, 2007.
Akhtar et al., *Trends in Cell Bio.*, 2:139, 1992.
Akhtar, In: *Delivery Strategies for Antisense Oligonucleotide Therapeutics*, 1995.
Akinc et al. *Nat. Biotechnol.*, 2008 May; 26(5):561-9, 2008.
Aldrian-Herrada et al., *Nucleic Acids Res.*, 26:4910-16, 1998.
Allerson et al., *J. Med. Chem.*, 48:901-904, 2005.
Alli et al., *Oncogene*, 24:39-46, 2005.
Alo et al., *Cancer*, 77:474-482, 1996.
Alo et al., *Tumori*, 85:35-40, 1999.
Ambros, *Cell*, 113(6):673-676, 2003.
Arap et al., *Cancer Res.*, 55(6):1351-1354, 1995.
Austin-Ward and Villaseca, *Revista Medica de Chile*, 126(7): 838-845, 1998.
Ausubel et al., In: *Current Protocols in Molecular Biology*, John, Wiley & Sons, Inc, NY, 1994; 1996.
Baichwal and Sugden, In: *Gene Transfer*, Kucherlapati (Ed.), Plenum Press, NY, 117-148, 1986.
Bakhshi et al., *Cell*, 41(3):899-906, 1985.
Bellus, *J. Macromol. Sci. Pure Appl. Chem.*, A31(1): 1355-1376, 1994.
Bentin and Nielsen, *Biochemistry*, 35:8863-8869, 1996.
Bentwich et al., *Nat. Genet.*, 37:766-770, 2005.
Bhat-Nakshatri et al., *Nucleic Acids Res.*, 37(14):4850-4861, 2009.
Blenkiron et al., *Genome Biol.*, 8:R214, 2007.
Boado et al. *J. Pharm. Sci.*, 87(11):1308-15, 1998.
Boado, *Adv. Drug Delivery Rev.*, 15:73, 1995.
Braasch et al., *Methods*, 23(2):97-107, 2001.
Brennecke et al., *Cell*, 113(1):25-36, 2003.
Bukowski et al., *Clinical Cancer Res.*, 4(10):2337-2347, 1998.
Burk et al., *EMBO Rep.*, 9:582-589, 2008.
Caldas et al., *Cancer Res.*, 54:3568-3573, 1994.
Caldas et al., *Nat. Genet.*, 8(1):27-32, 1994.
Calin et al., *Proc. Natl. Acad. Sci. USA*, 101:11755-11760, 2004.
Calin et al., *Proc. Natl. Acad. Sci. USA*, 99(24):15524-15529, 2002.
Carbonelli et al., *FEMS Microbiol. Lett.*, 177(1):75-82, 1999.
Carrington et al. *Science*, 301(5631):336-338, 2003.
Chang et al., *J. Exp. Med.*, 200:1359-1370, 2004.
Chang et al., *Nature*, 430(7001):785-789, 2004.
Chang et al., *Proc. Natl. Acad. Sci. USA*, 105:4477-4482, 2008.
Chen & Greene, *Mol. Cell. Biol.* 5:392-401, 2004.
Chen et al., *Biochem. Biophys. Res. Commun.*, 385:596-600, 2009.
Chen et al., *Fed. of Eur. Biochem Soc.*, 309:115-118, 1992.
Chen et al., *Genes Dev.*, 19:1288-1293, 2005.
Cheng et al., *Cancer Res.*, 54(21):5547-5551, 1994.
Cho, *Mol. Cancer*, 6:60, 2007.
Choung et al., *Biochem. Biophys. Res. Commun.*, 342:919-927, 2006.
Chowrira et al., *J. Biol. Chem.*, 269(41):25856-25864, 1994.
Christodoulides et al., *Microbiology*, 144(Pt 11):3027-3037, 1998.
Cleary and Sklar, *Proc. Natl. Acad. Sci. USA*, 82(21):7439-7443, 1985.
Cleary et al., *J. Exp. Med.*, 164(1):315-320, 1986.
Cocea, *Biotechniques*, 23(5):814-816, 1997.
Cochrane et al., *Mol. Cancer. Ther.*, 2009 [Epub ahead of print]
Coupar et al., *Gene*, 68:1-10, 1988.
Couture et al., *Trends in Genetics*, 12:510, 1996.
Cowland et al., *Apmis*, 115:1090-106, 2007.
Davidson et al., *J. Immunother.*, 21(5):389-398, 1998.
de Ronde et al., *Breast Cancer Res. Treat.*, 2009 [Epub ahead of print]
De Schrijver et al., *Cancer Res.*, 63:3799-3804, 2003.
Demidov et al., *ChemBiochem.*, 2:133-139, 2001.
Dogini et al., *J. Mol. Neurosci.*, 35(3):331-337, 2008.
Dostie et al., *RNA*, 9:180-186, 2003.
Duursma et al., *RNA*, 14 (5):872-877, 2008.
Egholm et al., *Nature*, 365(6446):566-568, 1993.
Elayadi et al., *Nucleic Acids Res.*, 29(8):1683-9, 2001.
Elmén et al., *Nature*, 452(7189):896-9, 2008.
Engels and Hutvagner, *Oncogene*, 25:6163-6169, 2006.
Esau et al. *Cell Metab.*, 3(2):87-98, 2006.

European Appln. 320 308
European Appln. 329 822
European Appln. 373 203
European Appln. 785 280
European Appln. 799 897
Fabbri et al, *Proc. Natl. Acad. Sci. USA*, 104:15805-15810, 2007.
Faruqi et al., *Proc. Natl. Acad. Sci. USA*, 95:1398-1403, 1998.
Fatkin et al., *J. Clin. Invest.*, 106(11):1351-1359, 2000.
Fodor et al., *Science*, 251:767-773, 1991.
Frieden et al., *Nucle. Nucleo. Nucleic Acids*, 22(5-8):1041-3, 2003.
Friedmann, *Science*, 244:1275-1281, 1989.
Frohman, In: *PCR Protocols: A Guide To Methods And Applications*, Academic Press, N.Y., 1990.
GB Appln. 2 202 328
Gregory et al., *Nat. Cell Biol.*, 10(5):593-601, 2008.
Griffiths-Jones et al., *Nucleic Acids Res.*, 34:D140-144, 2006.
Hacia et al., *Nature Genet.*, 14:441-449, 1996.
Haeberli et al., *Nucleic Acids Res.*, 33:3965-3975, 2005.
Hall et al., *Nucleic Acids Res.*, 32:5991-6000, 2004.
Hall et al., *Nucleic Acids Res.*, 34:2773-2781, 2006.
Halterman, *Pharmacotherapy*, 28:1255-1266, 2008.
Hanibuchi et al., *Int. J. Cancer*, 78(4):480-485, 1998.
Hassani et al., *J. Gene Med.*, 7(2):198-207, 2004.
Hellstrand et al., *Acta Oncologica*, 37(4):347-353, 1998.
Hermonat and Muzycska, *Proc. Natl. Acad. Sci. USA*, 81:6466-6470, 1984.
Hofland and Huang, *Handb. Exp. Pharmacol.*, 137:165, 1999.
Holstege et al., *EMBO J.*, 16:7468-7480, 1997.
Horwich et al. *J. Virol.*, 64:642-650, 1990.
Hoshika et al., *Nucleic Acids Res.*, 32:3815-3825, 2004.
Hui and Hashimoto, *Infection Immun.*, 66(11):5329-5336, 1998.
Hurteau et al., *Cancer Res.*, 67:7972-7976, 2007.
Hurteau et al., *Cell Cycle*, 8(13):2064-2069, 2009.
Hussussian et al., *Nat. Genet.*, 8(1):15-21, 1994.
Hutvagner et al., *PLoS Biol.*, 2(4):E98, 2004.
Innis et al., *Proc. Natl. Acad. Sci. USA*, 85(24):9436-9440, 1988.
Inouye and Inouye, *Nucleic Acids Res.*, 13:3101-3109, 1985.
Iorio et al., *Cancer Res.*, 65:7065-7070, 2005.
Iorio et al., *Eur. J. Cancer*, 44:2753-2759, 2008.
Ishiwata et al., *Chem. Phare. Bull.*, 43:1005, 1995.
Izant and Weintraub, *Science*, 229:345, 1985.
Jensen et al., *Mod. Pathol.*, 21:1413-1420, 2008.
Jolliet-Riant and Tillement, *Fundam. Clin. Pharmacol.*, 13:16, 1999.
Ju et al., *Gene Ther.*, 7(19):1672-1679, 2000.
Kahl et al., *J. Mol. Biol.*, 299:75-89, 2000.
Kaihatsu et al., *Biochem.*, 42(47):13996-4003, 2003.
Kaihatsu et al., *Chem. Biol.*, 11:749-758, 2004.
Kaklamani and Gradishar, Curr. Treat. Options Oncol., 7:123-128, 2006.
Kamb et al., *Nat. Genet.*, 8(1):23-26, 1994.
Kamb et al., *Science*, 2674:436-440, 1994.
Kashani-Sabet et al., *Antisense Res. Dev.*, 2:3, 1992.
Kaur et al., *Biochemistry*, 45(23):7347-7355, 2006.
Kerr et al., *Br. J. Cancer*, 26(4):239-257, 1972.
Kim et al., *Proc. Natl. Acad. Sci. USA*, 101:360-365, 2004.
Kiriazis and Kranias, *Annu. Rev. Physiol.*, 62:321-351, 2000.
Klinakis et al., *Proc. Natl. Acad. Sci. USA*, 106:2359-2364, 2009.
Korpal et al., *J. Biol. Chem.*, 283:14910-14914, 2008.
Koshkin et al., *Bioorg. Med. Chem. Lett.*, 8(16):2219-22, 1998.
Krenz and Robbins, *J. Am. Coll. Cardiol.*, 44:2390-2397, 2004.
Krützfeldt et al., *Nature*, 438:685-689, 2005.
Kumar et al., *Biochem. Pharmacol.*, 55:775-783, 1998.
Kumar et al., *Nat. Genet.*, 39:673-677, 2007.
Kwoh et al., *Proc. Natl. Acad. Sci. USA*, 86:1173, 1989.
Lagos-Quintana et al., *Curr. Biol.*, 12:735-739, 2002.
Lagos-Quintana et al., *Science*, 294(5543):853-858, 2001.
Landgraf et al., *Cell*, 129:1401-1414, 2007.
Larsen and Nielsen, *Nucl. Acids Res.*, 24:458-463, 1996.
Lasic et al., *Chem. Rev.* 95:2601, 1995.
Lasic et al., *Science*, 267:1275, 1995.
Lau et al., *Science*, 294(5543):858-862, 2001.
Law et al., *Cancer Res.*, 68:10238-10246, 2008.
Lee and Ambros, *Science*, 294(5543):862-864, 2001.
Lee et al., *Arch. Biochem. Biophys.*, 381:43-52, 2000.
Lerma et al., *Mod. Pathol.*, 20:1200-1207, 2007.
Levenson et al., *Hum. Gene Ther.*, 9(8):1233-1236, 1998.
Li and Carthew, *Cell*, 123:1267-1277, 2005.
Li et al., *Proc. Natl. Acad. Sci. USA*, 102:19231-19236, 2005.
Lim et al., *Science*, 299:1540, 2003.
Lin et al., *Intl. J. Cancer*, 123:372-379, 2008.
Liu et al., *Cancer Res.*, 55(14):3117-3122, 1995.
Lowery et al., *Clin. Cancer Res.*, 14:360-365, 2008.
Lowes et al., *J. Clin. Invest.*, 100(9):2315-2324, 1997.
Lu et al., *Nature*, 435:834-838, 2005.
Lui et al., *Cancer Res.* 67:6031-6043(2007
Mashima et al., *Br. J. Cancer*, 100:1369-1372, 2009.
Mattie et al., *Mol. Cancer*, 5:24, 2006.
Maurer et al., *Mol. Membr. Biol.*, 16:129, 1999.
McGarry and Lindquist, *Proc. Natl. Acad. Sci. USA*, 83:399, 1986.
McMahon et al., *Life Sci.*, 71(3):325-3, 2002.
Meche et al., *J. Morphol. Embryol.*, 50:217-221, 2009.
Meister et al., *Mol. Cell.*, 15:185-197, 2004.
Menendez and Lupu, *Arch. Immunol. Ther. Exp. (Warsz)*, 52:414-426, 2004.
Menendez et al., *Int. J. Cancer*, 115:19-35, 2005.
Miller et al., *J. Biol. Chem.*, 283:29897-29903, 2008.
Mitchell et al., *Ann. NY Acad. Sci.*, 690:153-166, 1993.
Mitchell et al., *J. Clin. Oncol.*, 8(5):856-869, 1990.
Miyata et al., *Circ. Res.*, 86(4):386-390, 2000.
Mollegaard et al., *Proc. Natl. Acad. Sci. USA*, 91:3892-3895, 1994.
Mori et al., *Cancer Res.*, 54(13):3396-3397, 1994.
Morita et al., *Bioorg. Med. Chem.*, 11(10):2211-26, 2003.
Morris and Carey, Rev. Endocr. Metab. Disord., 8:185-198, 2007.
Morris et al., *Science*, 305:1289-1292, 2004.
Morton et al., *Arch. Surg.*, 127:392-399, 1992.
Mukohara et al., *Cancer Lett.*, 282:14-24, 2009.
Nicolas and Rubinstein, In: *Vectors: A survey of molecular cloning vectors and their uses*, Rodriguez and Denhardt, eds., Stoneham: Butterworth, pp. 494-513, 1988
Nielsen et al., *Science*, 254:1497-1500, 1991.
Nobori et al., *Nature (London)*, 368:753-756, 1995.
Ohara et al., *Proc. Natl. Acad. Sci. USA*, 86:5673-5677, 1989.
Ohkawa et al., *Nucleic Acids Symp. Ser.*, 27:156, 1992.
Ojwang et al., *Proc. Natl. Acad. Sci. USA*, 89:10802, 1992.
Okamoto et al., *Proc. Natl. Acad. Sci. USA*, 91(23):11045-11049, 1994.

Oku et al., *Biochim. Biophys. Acta,* 1238:86, 1995.
Orlow et al., *Cancer Res,* 54(11):2848-2851, 1994.
Ouellet et al. *J. Biomed. Biotechnol.,* 2006(4):69616, 2006.
Pandey and Picard, *Mol. Cell Biol.,* 29:3783-3790, 2009.
Pardridge et al., *Proc. Natl. Acad. Sci. USA,* 92:5592, 1995.
Park et al., *Genes Dev.,* 22:894-907, 2008.
Paroo and Corey, *Trends Biotechnol.,* 22(8):390-4, 2004.
Pasquinelli and Ruvkun, *Ann. Rev. Cell Dev. Biol.,* 18:495-513, 2002.
Paterson et al., *ScientificWorld J.,* 8:901-904, 2008.
PCT Appln. PCT/US87/00880
PCT Appln. PCT/US89/01025
PCT Appln. WO 00/53722
PCT Appln. WO 01/38580
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100012
PCT Appln. WO 03/100448A1
PCT Appln. WO 04/020085
PCT Appln. WO 04/027093
PCT Appln. WO 05/021570
PCT Appln. WO 05/121371
PCT Appln. WO 05/115481
PCT Appln. WO 09/923,256
PCT Appln. WO 09/936,760
PCT Appln. WO 88/10315
PCT Appln. WO 89/06700
PCT Appln. WO 90/07641
PCT Appln. WO 93/17126
PCT Appln. WO 93/23569
PCT Appln. WO 94/02595
PCT Appln. WO 94/02595
PCT Appln. WO 94/14226
PCT Appln. WO 95/11995
PCT Appln. WO 95/21265
PCT Appln. WO 95/21944
PCT Appln. WO 95/35505
PCT Appln. WO 96/10390
PCT Appln. WO 96/10391
PCT Appln. WO 96/10392
PCT Appln. WO 96/31622
PCT Appln. WO 97/10365
PCT Appln. WO 97/27317
PCT Appln. WO 97/43450
PCT Appln. WO 98/39352
PCT Appln. WO 99/14226
PCT Appln. WO 99/35505
Pease et al., *Proc. Natl. Acad. Sci. USA,* 91:5022-5026, 1994.
Pietras et al., *Oncogene,* 17(17):2235-2249, 1998.
Poy et al., *Nature,* 432:226-230, 2004.
Prakash et al., *J. Med. Chem.,* 48:4247-4253, 2005.
Propulic et al., *J. Virol.,* 66:1432-1441, 1992.
Puig et al., *Breast Cancer Res. Treat.,* 109:471-479, 2008.
Qin et al., *Proc. Natl. Acad. Sci. USA,* 95(24):14411-14416, 1998.
Rakha and Ellis, *Pathology,* 41:40-47, 2009.
Rand et al., *Cell,* 123:621-629, 2005.
Ravindranath and Morton, *Intern. Rev. Immunol.,* 7: 303-329, 1991.
Ridgeway, In: *Vectors: A Survey of Molecular Cloning Vectors and Their Uses,* Rodriguez et al. (Eds.), Stoneham: Butterworth, 467-492, 1988.
Rosenberg et al., *Ann. Surg.* 210(4):474-548, 1989.
Rosenberg et al., *N. Engl. J. Med.,* 319:1676, 1988.
Saetrom et al., *Nucleic Acids Res.,* 35:2333-2342, 2007.
Sambrook and Russell, Molecular Cloning: A Laboratory Manual 3$^{rd}$ Ed., Cold Spring Harbor Laboratory Press, 2001.
Sambrook et al., In: *Molecular cloning: a laboratory manual,* 2$^{nd}$ Ed., Cold Spring Harbor Laboratory Press, Cold Spring Harbor, N.Y., 1989.
Sarver et al., *Science,* 247:1222-1225, 1990.
Scanlon et al., *Proc. Natl. Acad. Sci. USA,* 88:10591-10595, 1991.
Sempere et al. *Cancer Res.,* 67(24):11612-11620, 2007.
Serrano et al., *Nature,* 366:704-707, 1993.
Serrano et al., *Science,* 267(5195):249-252, 1995.
Sewer et al., *Bioinformatics,* 6:267, 2005.
Shoemaker et al., *Nature Genetics,* 14:450-456, 1996.
Singh et al., *J. Biol. Chem.,* 273:20354-20362, 1998.
Soutschek et al., *Nature,* 432(7014):173-178, 2004.
Stockmans et al., *Curr. Opin. Oncol.,* 20:614-620, 2008.
Summerton and Weller, *Antisense Nucleic Acid Drug Dev.;* 7(3):187-95, 1997.
Swinnen et al., *Biochem. Biophys. Res. Commun.,* 302:898-903, 2003.
Taira et al., *Nucleic Acids Res.,* 19:5125, 1991.
Taylor and Gercel-Taylor, *Gynecol. Oncol.,* 110:13-21, 2008.
Temin, In: *Gene Transfer,* Kucherlapati (Ed.), NY, Plenum Press, 149-188, 1986.
Thompson et al., *Nature Genet.,* 9:444-450, 1995.
Tsujimoto and Croce, *Proc. Natl. Acad. Sci. USA,* 83(14): 5214-5218, 1986.
Tsujimoto et al., *Nature,* 315:340-343, 1985.
Tyler et al. *Proc. Natl. Acad. Sci. USA,* 8; 96(12):7053-8, 1999b.
Tyler et al., *Am. J. Physiol.,* 277(6 Pt 1):L1199-204, 1999a.
UK Appln. 8 803 000
Urban-Klein, *Gene Ther.,* 12:461-6, 2005.
Vazquez-Martin et al., *J. Cell Biochem.,* 105:1147-1152, 2008.
Ventura et al., *Nucleic Acids Res.,* 21:3249, 1993.
Wahlestedt et al., *Proc. Natl. Acad. Sci. USA,* 97:5633-5638, 2000
Walker et al., *Proc. Natl. Acad. Sci. USA,* 89:392-396, 1992.
Watanabe et al., *Genes Dev.,* 20:1732-1743, 2006.
Webster et al., *J. Biol. Chem.,* 284:5731-5741, 2009.
Weerasinghe et al., *J. Virol.,* 65:5531, 1991.
Xu et al., *Curr. Biol.,* 13(9):790-795, 2003.
Yi et al., *Nature,* 452:225-229, 2008.
Young and Anderson, *Breast Cancer Res.,* 10:202, 2008.
Zeng et al., *Cancer Res.,* 62(13):3630-3635, 2002.
Zhang et al., *J. Biol. Chem.,* 275:24436-24443, 2000.
Zhang et al., *Proc. Natl. Acad. Sci. USA,* 105:7004-7009, 2008.
Zhao et al., *J. Biol. Chem.,* 283(45):31079-31086, 2008.

The invention claimed is:

1. A method of identifying "triple-negative" breast cancer in a subject comprising:
   (a) obtaining a breast cancer tissue sample from said subject; and
   (b) assessing said sample for one or more miRNAs selected from the group consisting of miR-193b, miR-34a, miR-301a, miR-148a and/or miR-15b;
   wherein decreased levels of one or more of miR-193b, miR-34a, miR-301a, miR-148a and/or miR-15b in said sample, as compared to a luminal breast cancer, indicates that said subject has a "triple-negative" breast cancer.

2. The method of claim 1, wherein said sample is a biopsy or resected tumor tissue.

3. The method of claim 1, wherein one, two, three or four of said miRNAs are assessed.

4. The method of claim 1, wherein each of miR-193b, miR-34a, miR-301a, miR-148a and miR-15b are assessed.

5. The method of claim 1, wherein one, two, three or four of said miRNAs are decreased.

6. The method of claim 1, wherein each of miR-193b, miR-34a, miR-301a, miR-148a and miR-15b are decreased.

7. The method of claim 1, wherein said subject is determined not to have "triple-negative" breast cancer, and further comprising administering to said subject a treatment for ER-positive breast cancer.

8. The method of claim 1, wherein said subject is determined to have "triple-negative" breast cancer, and further comprising administering to said subject a treatment for "triple-negative" breast cancer.

9. The method of claim 8, wherein if said subject exhibits reduced miR-193b, said subject is treated with a fatty acid synthase inhibitor.

10. The method of claim 9, wherein said inhibitor is miR-193b, c75 or Orlistat®.

11. The method of claim 8, wherein if said subject exhibits reduced miR-34a, said subject is treated with miR-34a.

12. The method of claim 8, wherein if said subject exhibits reduced miR-301a, said subject is treated with miR-301a.

13. The method of claim 8, wherein if said subject exhibits reduced miR-148a, said subject is treated with miR-148a.

14. The method of claim 8, wherein if said subject exhibits reduced miR-15b, said subject is treated with miR-15b.

* * * * *